United States Patent [19]

Fulkerson et al.

[11] Patent Number: 4,738,250

[45] Date of Patent: Apr. 19, 1988

[54] APPARATUS AND METHOD FOR MICRO-ELECTRIC MEDICAL STIMULATION OF CELLS OF LIVING ANIMAL TISSUE

[75] Inventors: Melvin A. Fulkerson, Burnsville; Wyman E. Jacobson, Minnetonka; Joseph P. Tretter, Minneapolis; John Van Dierendonck, Robinsdale, all of Minn.

[73] Assignee: Mems Technology, Incorporated, Minneapolis, Minn.

[21] Appl. No.: 782,427

[22] Filed: Oct. 1, 1985

[51] Int. Cl.$^4$ .............................................. A61N 1/36
[52] U.S. Cl. ...................................................... 128/421
[58] Field of Search ............... 128/419 R, 429 R, 422, 128/423 R

[56] References Cited

U.S. PATENT DOCUMENTS

| | | | |
|---|---|---|---|
| 3,645,267 | 2/1972 | Hagfors | 128/421 |
| 3,648,708 | 3/1972 | Haeri | 128/422 |
| 3,718,132 | 2/1973 | Holt et al. | 128/1 C |
| 4,088,141 | 5/1978 | Niemi | 128/421 |
| 4,102,348 | 7/1978 | Hihara et al. | 128/422 |
| 4,208,008 | 6/1980 | Smith | 128/419 PG |
| 4,255,790 | 3/1981 | Hondeyhen | 128/421 |
| 4,408,608 | 10/1983 | Daly et al. | 128/421 |
| 4,456,012 | 6/1984 | Lattin | 128/420 R |
| 4,520,825 | 6/1985 | Thompson et al. | 128/422 |
| 4,582,063 | 4/1986 | Mickiewicz et al. | 128/421 |

FOREIGN PATENT DOCUMENTS

| | | |
|---|---|---|
| 1422845 | 1/1976 | United Kingdom . |
| 1535413 | 12/1978 | United Kingdom . |
| 1575322 | 9/1980 | United Kingdom . |
| 1587665 | 4/1981 | United Kingdom . |

OTHER PUBLICATIONS

Alverez, Oscar M., "The Healing of Superficial Skin Wounds is Stimulated by External Electrical Current," *Journal of Investigative Dermatology*, vol. 81, pp. 144-148, 1983.

Bok, Lee, "Chronic Ulcers of the Skin," published by McGraw-Hill Book Company, 1985.

Cheng, Ngok, M. D., "The Effects of Electric Current or ATP Generation, Protein Synthesis and Membrane Transport in Rat Skin," *Clinical Orthopedics*, vol. 171, pp. 264-272.

Konikoff, J. J., "Electrical Promotion of Soft Tissue Repairs," *Annals of Biomedical Engineering*, vol. 4, pp. 1-5, 1976.

Mannheimer & Lampe, "Clinical Transcutaneous Electrical Nerve Stimulation," published by F. A. Davis Company of Philadelphia, Pa., 1984.

Mitchell, Peter, D. Ph.D., "Chemiosmotic Coupling in Oxidative and Photosynthetic Phosphorylation," *Biological Review*, vol. 41, pp. 445-502, 1966.

Mitchell, Peter D. Ph.D., "Vectorial Chemistry and the Molecular Mechanics of Chemiosmotic Coupling: Power Transmission by Proticity," presented at the Ninth CIBA Medal Lecture and published in *Biochemical Society Transactions*, vol. 4, pp. 400-430, 1976.

Wolcott, L. E. et al., "Accelerated Healing of Skin Ulcers by Electrotherapy: Preliminary Clinical Results," *Southern Medical Journal*, vol. 62, pp. 795-801, Jul. 1969.

*Primary Examiner*—William E. Kamm
*Attorney, Agent, or Firm*—Kinney & Lange

[57] ABSTRACT

A medical electrical apparatus impresses a bipolar, low frequency voltage wave form through spaced-apart electrodes, across a damaged area of living animal tissue to cause a low, bipolar, current to flow through the damaged area to increase the metabolic activity of viable cells in that area and hence to accelerate healing. The current flow is monitored and used to control the magnitude of the voltage wave to cause the magnitude of current flow to be within the desired parameters. The frequency, wave form and voltage of the impressed voltage wave and the current flow are all below a level which can damage typical living cells.

33 Claims, 3 Drawing Sheets

CROSSING PATTERN

CIRCUMFERENTIAL PATTERN

Fig. 5

| STEP 1 | STEP 2 | STEP 3 | STEP 4 | WAVE FORM POLARITY |
|--------|--------|--------|--------|---------------------|
| O.K | 500 | .9 | 00:50 | M +/− |

STEP 5 - Push START to begin Treatment :

ENTRY CHECK LIST

AFTER EACH STEP, PRESS ENTER

STEP 1 - PRESS ENTER

STEP 2 - RANGE = 100 TO 600 uA

STEP 3 - RANGE = 0.1 TO 0.5 Hz.

STEP 4 - RANGE = 20 SEC. TO 20 MIN.

CHECK ENTRIES
and
ELECTRODE PLACEMENTS

THEN

STEP 5 - PRESS 'START' KEY TO TREAT

ON/OFF   INTERRUPT

| 1 | 2 | 3 | START |
|---|---|---|-------|
| 4 | 5 | 6 | POL± |
| 7 | 8 | 9 | WAVE |
| CLEAR | 0 | ALTER | ENTER |

APPARATUS AND METHOD FOR MICRO-ELECTRIC MEDICAL STIMULATION OF CELLS OF LIVING ANIMAL TISSUE

BACKGROUND OF THE INVENTION

1. Field of the Invention

A portion of the disclosure of this patent document contains material which is subject to copyright protection. The copyright owner has no objection to the facsimile reproduction by anyone of the patent document or the patent disclosure, as it appears in the U.S. Patent and Trademark Office patent files or records, but otherwise reserves all copyright rights whatsoever.

This invention has relation to the use of an electrical treatment signal adapted for application to living animal tissue, including human tissue, to thereby induce electric current flow through cells of that tissue for the purpose of increasing the metabolic activity of the cells, and for the purpose of preventing further damage to cells in an area where cells have been initially damaged.

2. Description of the Prior Art

A chemiosmotic hypothesis has been promulgated by Peter D. Mitchell, Ph.D. Although Dr. Mitchell published a large number of papers in the scientific literature, an elucidation of this hypothesis, his life's work, was presented by him in THE NINTH CIBA MEDAL LECTURE and was published as follows: "Vectorial Chemistry and the Molecular Mechanics of Chemiosmotic Coupling: Power Transmission by Proticity." *Biochemical Society Transactions,* 1976, Vol. 4: Pgs. 400–430. To a substantial extent, this paper is an explanation of, an expansion of, and an updating of a paper published by him in 1966 entitled "Chemiosmotic Coupling in Oxidative and Photosynthetic Phosphorylation." *Biological Review* (1966), Vol. 41, Pgs. 445–502.

This hypothesis has now been widely accepted, and in 1976, Dr. Mitchell received the Nobel Prize for his work. The hypothesis was based on four fundamental postulates, as to the structural and functional systems involved in chemical and osmotic forces and by which proton-translocating mechanisms and proton-linked porter systems operate for cellular metabolism, through a topologically-closed insulating membrane, called the coupling membrane.

By translocating protons, a protonic potential differential is generated across the insulating membrane. This potential difference is quite similar to an electrical potential difference.

The chemiosmotic mechanism at the level of the cell membrane has sometimes been referred to as "the Mitchell pump", but not so designated by Dr. Mitchell.

Following the teachings of Dr. Mitchell, others have investigated the setting up of an electrical potential difference across areas of damaged epidermal and dermal tissue to study the effects of the flow of electrical currents through such tissue on the stimulation of metabolic activity. This includes the stimulation of the generation of adenosine triphosphate (ATP), protein synthesis, an accelerated cell membrane transport system, and an increase in the production of collagen.

Ngok Cheng, M.D. and his associates investigated some of these effects and published a paper entitled "The Effects of Electric Current on ATP Generation, Protein Synthesis and Membrane Transport in Rat Skin." *Clinical Orthopedics* 1982; Vol. 171, Pgs. 264–272.

Dr. Cheng and his colleagues reported some of the biochemical effects that occur in skin tissue of rats during in vitro stimulation with an electric current. Their method included the application of a direct electrical current to samples of tissue using currents that varied from one to 30,000 microamperes, usually for two to four hours at a constant temperature of 37° C. Separate strips of living rat skin were exposed for 2 hours to 10, 50, 100, 500, 1000 and 5000 microamperes direct current. These were then analyzed for ATP levels and compared with untreated (control) tissues. Their results indicated a five fold increase in ATP in tissue stimulated with 500 microamperes direct current.

Using one to 30,000 microamperes direct current to additional strips of rat tissue optimum incorporation of glycine into amino-acids, and subsequent synthesis of cell protein, occurred also at about 500 microamperes. Both ATP and protein synthesis fell off in a linear manner for tissue stimulated with 1000 to 5000 microamperes. At 5000 to 30,000 microamperes, protein synthesis did not occur, which findings suggested severe and/or lethal damage to the cells.

Oscar M. Alvarez, Ph.D. and his colleagues published a paper entitled: "The Healing of Superficial Skin Wounds is Stimulated by External Electrical Current." *Journal of Investigative Dermatology,* 1983; Vol. 81, Pgs. 144–148. Reported in this paper were the effects of direct electric current supplied by an energized silver-coated electrode on dermal and epidermal wound healing. Eleven young "Yorkshire" pigs were wounded, and a direct current was delivered by a silver-coated electrode directly over each wound through a wet dressing with the return electrode situated on another portion of the pig's body. A self-contained, battery-operated generator was a source of "constant current." The current was applied as steady state direct current for 24 hours at a time over a seven day term. During each 24 hour period, "the current intensity decreased linearly from 300 microamperes upon initial connection to 50 microamperes at the end of a 24 hour treatment period." A large increase in "labeled collagen" was noticed but not until four and five days after wounding.

Other work in the prior art is discussed in each of the foregoing papers, and is listed in the bibliography of each of these four papers.

A paper by J. J. Konikoff entitled: "Electrical Promotion of Soft Tissue Repairs"; *Annals of Biomedical Engineering,* Vol. 4, Pgs. 1–5 (1976) reported on the tensile strength of excised skin/incisions in rabbits that had been cut, and subjected to a 20 microampere current flow through the incisions for seven days. This current flow was direct and applied, apparently, without change of direction for the entire seven day test. Favorable results were obtained as to the strength of the treated skin/incisions compared to the untreated (control) incisions.

Other related papers, apparently also dealing with direct current applied over extended time period include the following: Wolcott, L. E. et al "Accelerated Healing of Skin Ulcers by Electrotherapy: Preliminary Clinical Results", *Southern Medical Journal,* Vol. 62, Pgs. 795–801 and bibliography cited therein.

This paper by Wolcott et al, after summarizing the problems faced in connection with bedsores or decubitus ulcers and other ischemic skin ulcers, goes on to characterize the state of the art prior to the present invention quite accurately as follows: "Historically, remedies have been distinguished by their ingenuity, variety and rather uniform ineffectiveness."

The literature relating to transcutaneous electrical nerve stimulation (TENS) and related to chronic ulcers of the skin has been consulted for possible pertinence to the present invention, and nothing pertinent has been located. For example, a book entitled: "Clinical Transcutaneous Electrical Nerve Stimulation" by Mannheimer and Lampe, has been published by F. A. Davis Company of Philadelphia, ©1984. It shows the present state of the art in the TENS field to be the use of spiked waveform electrical energy "bursts" of sufficient magnitude and duration to cause muscle twitching and contractions. The currents involved are several orders of magnitude greater than the currents utilized in the present invention.

A book "Chronic Ulcers of the Skin" by Y. Lee Bok, published by McGraw-Hill Book Company, ©1985, does not even refer to electrical stimulation. Dr. Bok is a recognized authority in his field.

No reference in either book was found which appeared pertinent to the present invention.

A computerized search of the literature relating to this invention has been made; but turned up nothing any more pertinent than the prior art discussed above.

As is evident from the above references, medical techniques for treating soft living animal tissue through the application of electrical energy have only recently been studied. All of the studies to date appear to use a unidirectional current flow. There are, however, detrimental side effects associated with this technique. Galvanic effects associated with unidirectional current flow can, for example, cause cell damage and loss of tissue integrity.

There is clearly a continuing need for improved medical techniques for treating such tissue. Electrical techniques appear to hold great promise. Improvements to known techniques which significantly increase treatment results would be especially desirable. Such techniques should employ current flows which do not have other adverse effects on living animal (including human) tissues, the cells which make up such tissues, or other biologic systems. To be avoided are current flows causing stress-electricity (piezoelectricity), excessive heat (pyroelectricity), electrical polarization, electrical double layering, or electrophoresis (field differential).

The instrument used to implement these techniques must, of course, be safe to use. The instrument should also be easy for clinicians to operate.

The inventors and those in privity with them are now aware of no prior art which is closer than that set out above; and are aware of no prior art which negates the patentability of the claims made herein.

SUMMARY OF THE INVENTION

The electrical medical instrument of the invention is for increasing metabolic activity of desired cells of living tissue by producing an electrical treatment signal adapted for application to the tissue to thereby induce electrical current flow through the cells to be treated.

This increase in metabolic activity results in at least the following positive benefits: accelerated production of adenosine triphosphate (ATP), increased synthesis of cell protein, improved cell membrane transport system, and accelerated production of collagen.

Additionally, this electrical treatment signal reduces the concentration of free radicals which appear when cells are damaged. These free radicals are known to cause further damage by cell membrane disruption; and this reduction, done in accordance with the teachings of the invention, tends to reduce or eliminate this continuing damage without the current flow itself damaging the cells or otherwise insulting the living tissue being treated.

The electrical medical treatment apparatus and instrument of the invention can include a source of direct electrical energy of predetermined voltage. A pair of output terminals are connected to a pair of electrodes which are adapted to be placed in contact with healthy tissue opposite one another across damaged tissue, for example; and means is provided for generating from the energy source a voltage wave of predetermined shape and magnitude and impressing it across the output terminals. The power is held below that at which a cell to be treated can be damaged, and the wave form of the voltage wave is such that it and the resulting current flow will not damage or otherwise insult living tissue when impressed across that tissue.

To accomplish its purposes, the instrument includes a means for producing a periodic electrical treatment signal at a desired treatment signal frequency for a desired treatment signal time period. The treatment signal is characterized by first and second electrical parameters. The instrument also includes means for receiving information representative of a selected value of the first electrical parameter of the treatment signal; means for monitoring the first electrical parameter of the treatment signal; and means responsive to the means for receiving information and the means for monitoring the first electrical parameter for causing the second parameter of the treatment signal to increase during each treatment signal time period until the first parameter of the treatment signal attains the selected value, and for maintaining the first parameter of the treatment signal at the selected value for a remainder of such preselected treatment signal time period.

In the form of the invention as shown, the first electrical parameter is the current of the treatment signal, and the means for producing the treatment signal causes the second electrical parameter to be the voltage of the treatment signal. Without limiting the general coverage of the concept involved, the means for producing the treatment signal, in the form of the invention as shown, can cause the magnitude of the current of the treatment signal to be within a range of about 20 to 900 microamperes; and the means for producing the treatment signal causes the magnitude of the voltage of the treatment signal to be within a range of from zero to 30 volts.

The means for producing the treatment signal produces a bipolar treatment signal having a treatment signal frequency to be within a range of about 0.1 to 15 Hz.

In one form of the invention, the means for producing a treatment signal causes a treatment activation period to be within a range of about 20 seconds to about twenty minutes.

In a first embodiment of the invention, the means for causing the second parameter of the treatment signal to increase causes the second parameter of the treatment signal to increase linearly during each treatment signal time period until the first parameter of the treatment signal attains its preselected value; and in a second embodiment of the invention, the means for causing the second parameter of the treatment signal to increase causes the second parameter to increase nonlinearly during each treatment signal time period until the first parameter of the treatment signal attains its preselected value. In this second form of the invention, the means for causing the second parameter of the treatment signal to increase causes the second parameter of the treatment signal to increase as an exponential function during each treatment signal time period until the first parameter of the treatment signal attains its preselected value.

A method of increasing the metabolic activity of preselected cells and living animal tissue, including, for example, damaged human tissue, includes the steps of situating a pair of spaced-apart electrodes in contact with healthy animal tissue on opposite sides of an area containing damaged cells and containing cells to be treated and stimulated; and externally inducing a flow of electrical current between the electrodes through the treatment area by impressing an external bipolar voltage wave across the electrodes at a frequency of between 0.1 and 1.0 Hz. Effective results have been obtained when the voltage impressed between the electrodes is so regulated that the current flow resulting from the steps set out above does not exceed 900 microamperes.

In order to stimulate the most metabolic activity of the most cells, the electrodes are activated by a bipolar voltage wave having a frequency of slightly less than 1.0 Hz, bipolar for a period of at least 20 seconds, and then the electrodes are repositioned and the voltage wave reapplied. This repositioned placement can be done by moving the electrodes on generally parallel paths with respect to each other starting at one end of the damaged area and moving to the other. Then for each treatment session, the current paths between electrodes during each successive placement will lie on lines parallel to each other.

Another way of positioning the electrodes to treat the entire damaged area is to move the electrodes in, for example, a counterclockwise direction between placements such that each current path between the electrodes during each successive placement period will lie on a line passing near or through the center of the damaged area, and these lines, taken together, will resemble the spokes of a wheel.

BRIEF DESCRIPTION OF THE DRAWINGS

FIG. 5 is a plan view of an instrument panel of the instrument of FIG. 1 as it and the liquid crystal display (LCD) forming a part of it will appear just prior to initiating a treatment activation time period.

DETAILED DESCRIPTION OF THE PREFERRED EMBODIMENTS

Figure 1:
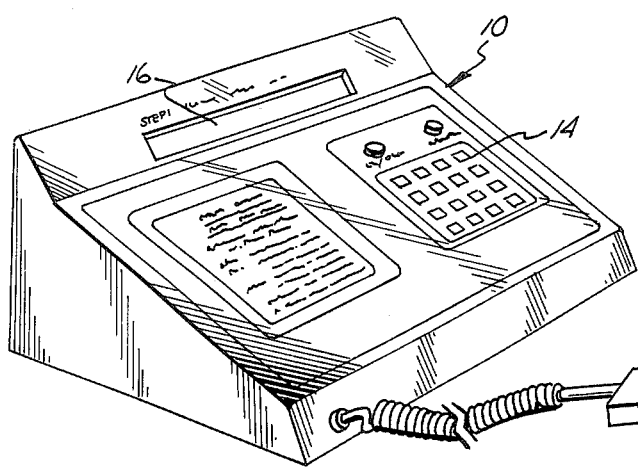
FIG. 1 is a perspective view of a medical instrument and other apparatus for micro-electric medical stimulation of cells of living animal tissue showing the relationship of two electrodes forming a part of that apparatus with respect to living animal tissue to be stimulated.

An electrical medical treatment instrument 10 includes a microcomputer 12, a key pad 14 for entering information relative to desired parameters into the microcomputer and for activating and deactivating a treatment activation time period, a liquid crystal display (LCD) 16 for displaying the status of the operation of the instrument at each point in time, a pair of output terminals 18 and 19, an analog amplifier/driver 20 for impressing a controlled voltage wave across the terminals 18 and 19 for controlled treatment activation time periods, a digital-to-analog converter 22 for transmitting control signals from microcomputer 12 to amplifier/driver 20, a current monitor 24 for reading the current flowing through the output terminals 18 and 19, and an analog-to-digital converter 26 to transmit information relative to this current flow information from monitor 24 to the microcomputer so that the microcomputer can supply information to the digital-to-analog converter 22 to control the signal to the amplifier/driver so that the voltage wave will be such as to keep the current flow within the desired parameters.

Apparatus 28 of the invention includes not only the electrical medical treatment instrument 10 and all of its components as above described, but also first and second electrodes 30 and 31 each having a replaceable electrode pad 32 of any or unusual preferred construction, and lead wires 34,34, each extending between one of the output terminals 18 and 19 and one of the electrodes 30 and 31.

A direct current power supply 27 within the instrument 10 powers the microcomputer and the other elements of the instrument and its output is controlled to generate the output voltage wave as needed. It also forms part of the apparatus 28.

The method of the invention includes placing first electrode 30 and second electrode 31 (and pads 32) in electrical contact with two spaced-apart healthy portions of living animal tissue (including living human tissue) and impressing a bipolar voltage wave of very low frequency between the electrodes to cause a very low current flow through the living tissue between the electrodes, the wave form, frequency and current density of such flow being such that a typical cell in the path of such flow will not be damaged or otherwise insulted.

This carefully limited and controlled current flow will tend to increase the metabolic activity of all healthy cells in living tissue which come within the path of any of such current flow, tending to causing such cells to divide, thus replacing any adjacent cells which are fatally damaged and encouraging healthy growth and/or regrowth of such living tissue.

Early experimentation with the apparatus and method of the invention has been in conjunction with the treatment of dicubital ulcers. However, the invention will be effective in treating areas of damaged or otherwise insulted living animal tissue from many different causes, and in increasing the metabolic activity of cells in apparently healthy areas of living tissue. By way of example, and not by way of limitation, the invention is effective in treating burns of all degrees from the light sunburn of a first degree through very severe third degree burns, wounds resulting from cutting, abrasion, bruising, gunshot, etc.

When individual cells are damaged, substantial concentrations of atoms and groups of atoms each having at least one unpaired electron result. If these free radicals are not somehow supplied with their "missing" electrons, they can be disruptive of adjacent healthy cells over a period of time following the initial damage and their creation. The current flow induced by the apparatus and method of the present invention serves to supply the needed electrons to these free radicals, reducing or eliminating their threat to adjacent healthy cells.

Figure 3:
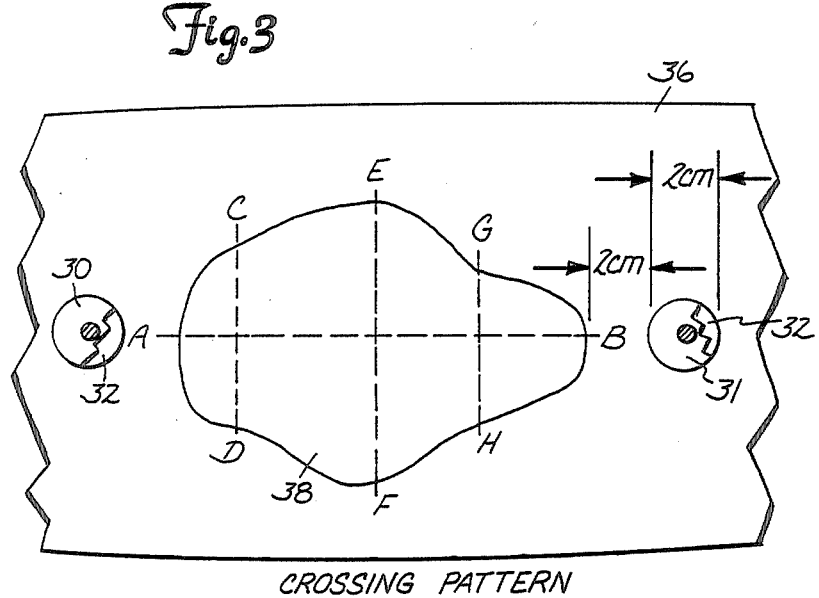
FIG. 3 is a schematic representation of an area of damaged living human tissue within a healthy area of such tissue and illustrating a crossing pattern for successive placement of the electrodes of the apparatus of the invention for the treatment of such damaged area.
Figure 4:
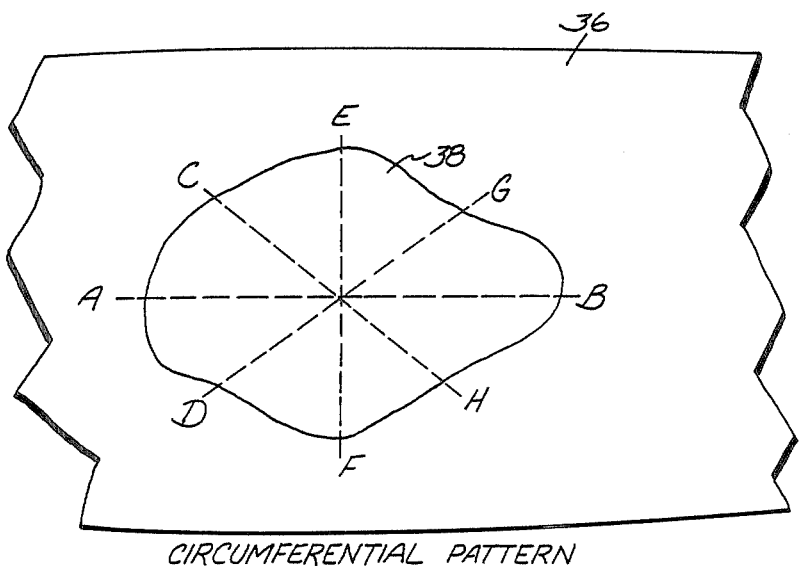
FIG. 4 is likewise a schematic representation of a damaged area of living animal tissue within a healthy area of such tissue but illustrating a circumferential pattern for the placement of such electrodes for such purpose.
Figure 2:
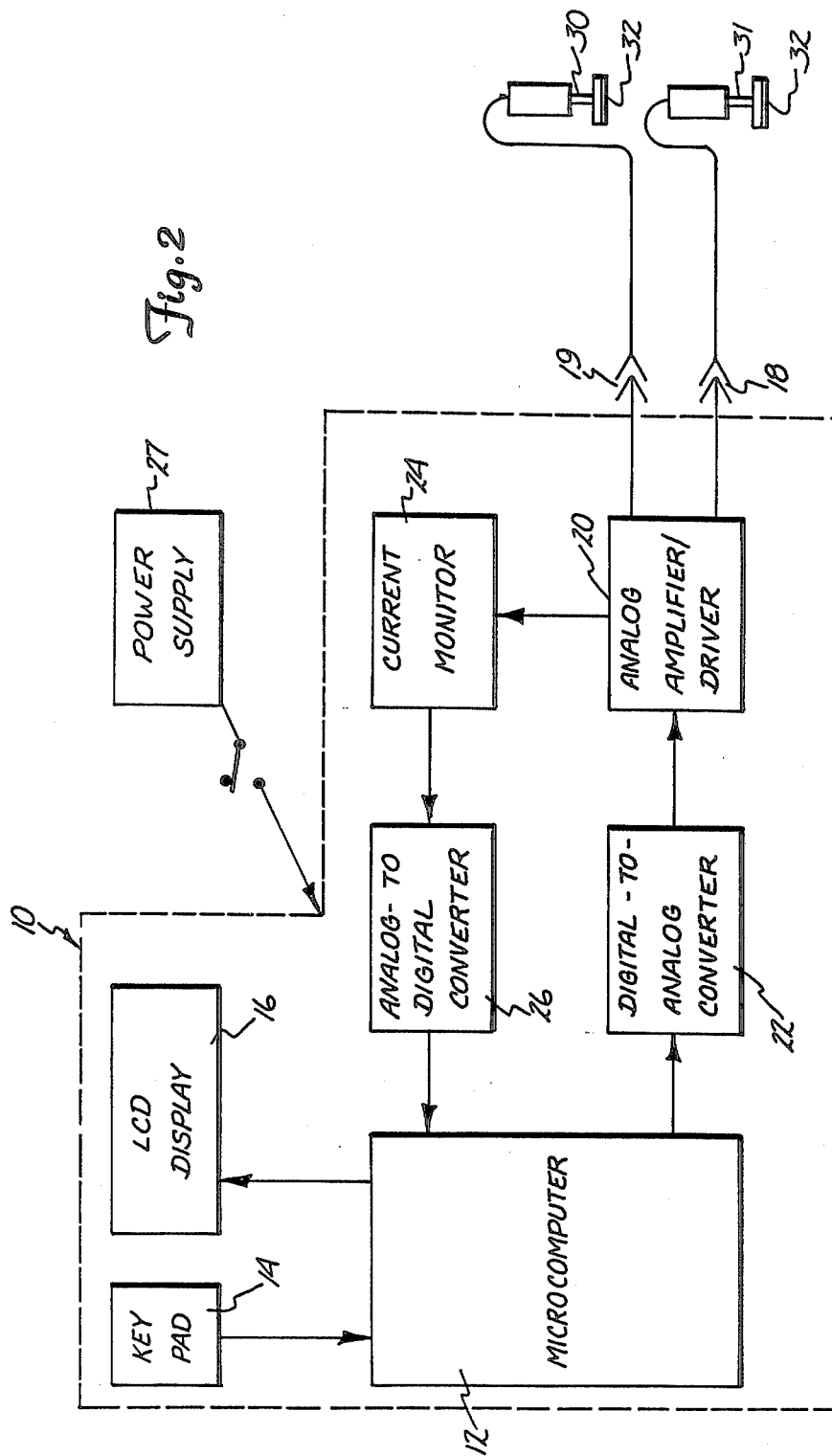
FIG. 2 is a block diagram of the electrical components of the apparatus of FIG. 1.

For purposes of illustration and example, and without limitation, FIGS. 1, 3 and 4 more or less diagrammatically illustrate surface areas covering healthy living tissue 36 and areas of damaged living tissue and cells 38 within the living tissue.

In use, electrodes 30 and 31 are placed in electrical contact with healthy living tissue on opposite sides of the damaged living tissue and cells to be treated at position, for example, as indicated in FIG. 3. As indicated, these electrodes (and pads 32) present a circular area of approximately 2 centimeters (cm) in diameter in contact with the surface of the healthy living tissue 36, and are situated approximately two cm from the area 38 of the damaged tissue. However, other configurations of electrodes, electrode pads 32 and other placements can be used within the spirit and scope of the invention as long as a current path is provided through the living tissue to be treated between the two electrodes.

With the electrodes so positioned, a voltage wave form is impressed across the electrodes 30 and 31 through the instrumentality of the electrical medical treatment instrument 10 for a preselected treatment activation period of time. Favorable results can be obtained when this activation time period is less than 20 seconds or as long as 20 minutes. Longer or shorter time periods appear to have no detrimental effects when the voltage wave is applied in accordance with the other teachings of the invention.

While experimentation on the use of unipolar voltage wave forms for particular applications continues, use of bipolar wave forms have proved to be especially effective and to be devoid of the problems mentioned above in connection with the use of direct current not in the form of a bipolar wave.

The frequency of the bipolar wave form used can be varied from a very low frequency to a frequency slightly less than 1 Hz. Good results have been obtained between 0.1 Hz and 0.9 Hz, and optimum results have been obtained using a frequency of 0.5 Hz.

The wave forms used can be from a group of wave forms, designated herein as "square wave" forms wherein the voltage rises in a linear fashion until a predetermined current flow is reached and then is maintained until the end of a treatment signal time period which is the half cycle determined by the selected frequency; and a group of waves designated herein as "modified square waves" wherein the voltage increases as an exponential function until the predetermined current flow reaches the predetermined level and is held at that level until the end of that half treatment signal time period.

The method of the invention calls for inducing a bipolar current flow between electrodes through the animal tissue to be treated, and limiting the maximum magnitude of that flow to below a level which can do damage to a typical cell in the path of the flow. Currents of from 20 to 900 microamperes maximum have been proved effective, currents between 20 and 600 microamperes give good results, while a current of between 500 and 600 microamperes provides optimum results. Current flows approaching 1000 microamperes or 1 milliampere have proved destructive to cells in the pathway of such flow.

For the purposes of research and experimentation, the instrument can be provided with switch means to produce not only the bipolar full wave form as discussed above, but also halfway forms of positive polarity or of negative polarity. This facility allows for the opportunity to obtain test data on unipolar wave forms which can be compared with the data and results obtained using the preferred bipolar wave form. To date use of the bipolar wave form has proved much superior.

The treatment instrument 10 provides a current flow between electrodes 30 and 31 which meet the predetermined criteria. If the measured parameters differ from the parameters selected by plus or minus 15%, the microcomputer will cause the particular treatment sequence to be aborted by dropping the voltage potential across electrodes 30 and 31 to zero. Similarly, should parameters outside of the appropriate ranges be selected by the operator, the selection will be rejected, and an audible and visual signal will indicate that an unacceptable parameter has been signaled.

To operate the instrument, the power supply 27 will be turned on to supply battery power to and throughout the instrument 10 by operation of an "ON/OFF" switch 40 accessible at the key pad 14. If the battery power is too low for operation, the lower level of the LCD 16 will read:

LOW BATTERY

If the battery power is adequate, the lower level of the LCD 16 will read:

STEP 1—SYSTEM SELF CHECKING—PRESS ENTER

If the instrument is ready to function properly, the upper level of the LCD 16 will signal "O.K." under the legend STEP 1 and the lower half will read:

STEP 2—ENTER uAMP

An appropriate number of microamperes will be entered by pressing the appropriate numbered keys on the key pad, for example, 500. Then the "ENTER" key will be pressed. The microamperes, in this case 500, will appear in the upper half of the LCD under the legend STEP 2 and the lower half of that display will read:

STEP 3—ENTER FREQUENCY

An appropriate frequency such as 0.9 Hz is entered by pressing the "9" key on the key pad and also the "ENTER" key. In addition to the signal "O.K." under STEP 1, and the entry "500" under STEP 2, the LCD will now display "0.9" under STEP 3, and the notation on its lower half will read:

STEP 4—ENTER TIME

An appropriate treatment activation period time, such for example, as 50 seconds will be indicated by activation of keys 0050 on the key pad. After the "ENTER" key has been pressed, the notation "00:50" will appear under STEP 4, and the bottom half of the LCD will read:

STEP 5—PUSH START TO BEGIN TREATMENT

When the instrument is first turned on, the wave form selected from the wave form patterns stored in the microcomputer will be that of a "modified square wave," and the letter "M" will appear under the legend WAVE FORM. If a "square wave" form is desired, the "WAVE" button will be pressed once, changing the LCD under the notation "wave form" from an "M" (modified square wave) to an "S" (square wave).

When the machine is turned on, the notation "+/−" will appear on the LCD under the legend POLARITY and a full bipolar wave of the selected form will be utilized by the microcomputer in supplying potential across the output terminals 18 and 19. Pressing the "Pol +/−" key one time will cause the microcomputer to cause generation of a positive (+) half wave form, while pressing that key a second time will cause a negative (−) wave form to be generated. Operation of that key for the third time will return the instrument to the bipolar (+/−) operation.

The microcomputer 12 is programmed to continue operation as long as specific parameters are within specific, preselected ranges. For example, magnitude of current flow, magnitude of voltage of treatment signal, treatment signal frequency. When any such parameter moves out of its preselected range, the treatment will be aborted by the microcomputer causing the voltage across terminals 18 and 19 returning to zero. Such an abort sequence can occur because, for example, the electrodes are not connected to the terminals, because electrodes are spaced too far apart, because of abnormally low resistance, and for other reasons.

Should a parameter outside the preselected range be pressed into the key pad 14 by a clinician, it will not be accepted by the microcomputer as programmed, and the display will so indicate.

Typically the resistance of the current path between electrodes through healthy skin and other healthy living tissue is relatively high with respect to the resistance to current flow of the current path between electrodes which passes through an area of damaged cells of living tissue. In a usual case, the greater the damage, the lower the resistance to current flow between two electrodes placed in contact with the living tissue on opposite sides of the damaged area. The resistance in the current path between two equally spaced electrodes on the dry skin of different persons or even on different parts of the body of the same person will vary. Likewise, the resistance to current flow between two electrodes on opposite sides of a damaged area will also vary from one placement of electrodes to the next as the electrodes are moved after each successive activation period to insure that the entire damaged area receives the benefits of the treatment. Therefore, in order to treat the living animal tissue, including the cells adjacent to permanently damaged cells, with a bipolar current flow of a precisely defined magnitude as that flow is generated by a voltage wave of predetermined shape, it is necessary that the current flowing through the terminals 18 and 19 and consequently the current flowing between those terminals through the living animal tissue be monitored by the instrument. Based on the information received by the microcomputer from the current monitor, the microcomputer will cause the appropriate voltage wave form or treatment signal to be generated to keep the current flow within the desired range at all times.

To reduce the functions of the instrument 10 to its basic terms, the treatment signal is characterized by first and second electrical parameters. In this particular case, the first electrical parameter is the current of the treatment signal and the second electrical parameter is the voltage of the treatment signal.

The microcomputer 12, digital-to-analog converter 22 and analog amplifier/driver 20 together are programmed for producing a plurality of periodic electrical treatment signals at a treatment signal frequency, each treatment signal existing for a treatment signal time period which is an inverse function of that frequency. The microcomputer, the key pad 14 and the LCD 16 together provide a means for receiving information representative of a selected value of the first electrical parameter or current of the treatment signal. The current monitor 24 is a means for monitoring the first electrical parameter or current of the treatment signal. The microcomputer 12, the digital-to-analog converter 22 and the analog amplifier/driver 20 together provide means responsive to the means for receiving information and the means for monitoring the first electrical parameter (current) for causing the second parameter (voltage) of the treatment signal to increase during each treatment signal time period until the first parameter of the treatment signal attains the selected value, and for maintaining the first parameter of the treatment signal at the selected value for the remainder of such treatment signal time period.

In order that an entire damaged area of animal tissue and the cells in that area receive the current flow of the invention during each treatment session, electrodes 30 and 31 will have a number of different placements, each for a predetermined activation period, during each session. Any one of a number of different schedules for placements may be used effectively so long as the current path flowing during all of the activation periods includes substantially the entire area (for example the damaged area) to be treated. Two such schemes or systems for placement of the electrodes during successive activation periods will be understood by consideration of FIGS. 3 and 4.

In FIG. 3, a crossing pattern for electrode placement during each activation period is suggested. After a first placement of electrodes 30 and 31 adjacent points A and B as seen in FIG. 3 for a first treatment activation period, a second placement will be made with each of the electrodes in contact with healthy living animal tissue about two centimeters away from the damaged area and in position such that the line between the electrodes will coincide with the line CD. The next placement of the electrodes will be the same distance from the damaged area and in alignment with line EF, while a fourth placement of electrodes, similarly spaced from the damaged area, will be in alignment with line GH. This crossing pattern is the preferred pattern.

However, sometimes the position of the damaged area on the human body, for example, will make it easier and more effective to use a circumferential pattern of electrode placements as suggested in FIG. 4. Here the electrodes will also be placed in contact with healthy tissue about two centimeters from the damaged tissue and each placement successively to be in alignment with lines AB; CH; EF; and DG.

A suitable program for use in the microprocessor is as follows.

Although the present invention has been described with reference to preferred embodiments, workers skilled in the art will recognize that changes may be made in form and detail without departing from the spirit and scope of the invention.

```
*
*   MEMS MICROCODE
+---------------------------------------------------------------+
*                   KEY CODE DEFINES                             *
*                                                                *
*                                   SCAN OUT LINES               *
*                                                                *
*                                                                *
*                                  Y4  Y3  Y2  Y1                *
*                           BITS    0   1   2   3                *
*                SCAN IN LINES      |   |   |   |                *
*                     X1      7 —   1   2   3  STRT              *
*                     X2      6 —   4   5   6  POL               *
*                     X3      5 —   7   8   9  WFORM             *
*                     X4      4 —  CLR  0  ALT ENTR              *
*                                                                *
*        1 - 71h    2 - 72h   3 - 74h    STRT  - 78h             *
*        4 - 81h    5 - 82h   6 - 84h    POL   - 88h             *
*        7 - D1h    8 - D2h   9 - D4h    WFORM - D8h             *
*      CLR - E1h    0 - E2h ALT - E4h    ENTR  - E8h             *
*                                                                *
+---------------------------------------------------------------+
*
*       EQUATES
*
PORT1C  EQU     0           * PORT 1 CONTROL ADDRESS
PORT1D  EQU     2           * PORT 1 DATA ADDRESS
PORT2D  EQU     8000        * DAC MS DATA PORT
PORT2C  EQU     8001        * CONTROL PORT A
PORT3D  EQU     8002        * DAC LS DATA PORT
PORT3C  EQU     8003        * CONTROL PORT B
PORT4C  EQU     01          * BEEPER PORT CONTROL
PORT4D  EQU     03          * BEEPER PORT DATA (BITS 3,4)
DISPC   EQU     6001        * CONTROL PORT FOR DISPLAY
DISPD   EQU     6000        * DATA PORT FOR DISPLAY
VOLTG   EQU     A007        * ADC ADRS FOR OUTPUT VOLTAGE READING
BATTRY  EQU     A000        * ADC ADRS FOR BATTERY VOLTAGE READING
ENTERC  EQU     E8          * ENTER CHARACTER CODE
CLEARC  EQU     E1          * CLEAR CHARACTER CODE
STARTC  EQU     78          * START CHARACTER CODE
TIMER   EQU     09          * FREE RUNNING COUNTER
T_CMPR  EQU     0B          * TIMER COMPARE REGISTER
T_CTRL  EQU     08          * TIMER CONTROL REGISTER
CK_CSR  EQU     19          * CURSOR LOCATION OF CLOCK DISPLAY (LSD)
IO_CSR  EQU     58          * CURSOR LOCATION OF CURRENT OUTPUT (LSD)
*
*       VECTORS
*
        ORG     FFEE
*
FFEE    TRAP    RMB     $ E1FF      * FETCH/OPCODE ERROR INTERRUPT
*
        ORG     FFF0
*
```

```
FFF0    SCI     FDB     $ FB80          * SERIAL COMMUNICATIONS INTERFACE
FFF2    TOF     FDB     $ FB80          * TIMER OVERFLOW
FFF4    OCF     FDB     $ FB20          * TIMER OUTPUT COMPARE
FFF6    ICF     FDB     $ FB80          * TIMER INPUT COMPARE
FFF8    IRQ1    FDB     $ E449          * INTERRUPT REQUEST
FFFA    SWI     FDB     $ FB80          * SOFTWARE INTERRUPT
FFFC    NMI     FDB     $ FB00          * NON-MASKABLE INTERRUPT
FFFE    RES     FDB     $ E1FF          * RESET
*
*       VARIABLE DEFINES
*
*       ORG     80
*
0080    KEYHLD  RMB     1               * DEBOUNCE KEY SAVE LOCATION
0081    TEMP1   RMB     1               * BYTE SAVE LOCATION
0082    CHARCT  RMB     1               * INPUT BUFFER CHARACTER COUNTER
0083    TEMP2   RMB     2               * WORD SAVE LOCATION
0085    TEMPLT  RMB     2               * POINTER TO INPUT TEMPLATE
0087    BUFPTR  RMB     2               * POINTER TO INPUT BUFFER LOCATION
0089    TEMP2A  RMB     2
008B    POLS    RMB     1               * STATUS OF POLARITY TYPE ON DISPLAY
008C    WFORMS  RMB     1               * STATUS OF WAVEFORM ON DISPLAY
008D    INCVAL  RMB     2
008F    LASMAX  RMB     1               * HIGHEST VALUE OF io IN CURRENT SESSION
*
*
0080    FQ_MUL  EQU     KEYHLD          * REDEFINE VARIABLE NAMES FOR WAVE FORM GENERATION
0082    COUNT   EQU     CHARCT
0085    V_TBL   EQU     TEMPLT
0087    TBLEND  EQU     BUFPTR
0089    DACVAL  EQU     TEMP2A
*
        ORG     90
*
0090    INBUF   RMB     6               * INPUT BUFFER
0096    XHOLD   RMB     2               * XREG HOLD FOR INTERRUPT ROUTINE
*
*
*
        ORG     A0
*
00A0    VOLTS   RMB     2               * VARIABLES SET BY USER INPUT
00A2    AMPS    RMB     2
00A4    HERTZ   RMB     2
00A6    TIME    RMB     2
00A8    IOMAX   RMB     2               * MAX SELECTED CURRENT
00AA    TMPACC  RMB     1               * TEMPORARY ACCUMULATOR
*
*
*
*
*       MESSAGE DEFINITIONS
*
        ORG     $FC00
*
FC00 2B 2F 2D           BI_FAZ  DB      "+/-"
     00                         DB      00
```

```
‡
FC04  2B 20 20          POS_WV   DB      "+ "
      00                         DB      00
‡
FC08  20 20 2D          NEG_WV   DB      " -"
      00                         DB      00
‡

‡
FC2F  54 52 45 41 54    EMSG_I   DB      "TREATMENT INTERRUPTED - Push CLEAR"
      4D 45 4E 54 20
      49 4E 54 45 52
      52 55 50 54 45
      44 20 2D 20 50
      75 73 68 20 43
      4C 45 41 52
      00                         DB      00
‡
FC52  53 54 45 50 20    EMFMSG   DB      "STEP 1 - Enter EMF (40/50/60): "
      31 20 2D 20 45
      6E 74 65 72 20
      45 4D 46 20 28
      34 30 2F 35 30
      2F 36 30 29 3A
      20
      00                         DB      0
‡
FC72  53 54 45 50 20    AMPMSG   DB      "STEP 2 - Enter uAMP (20-90/100-600): "
      32 20 2D 20 45
      6E 74 65 72 20
      75 41 4D 50 20
      28 32 30 2D 39
      30 2F 31 30 30
      2D 36 30 30 29
      3A 20
      00                         DB      0
‡
FC98  53 54 45 50 20    FRQMSG   DB      "STEP 3 - Enter FREQUENCY (.1-10): "
      33 20 2D 20 45
      6E 74 65 72 20
      46 52 45 51 55
      45 4E 43 59 20
      28 2E 31 2D 31
      30 29 3A 20
      00                         DB      0
‡
FCBB  53 54 45 50 20    TIMMSG   DB      "STEP 4 - Enter TIME of treatment: "
      34 20 2D 20 45
      6E 74 65 72 20
      54 49 4D 45 20
      6F 66 20 74 72
      65 61 74 6D 65
      6E 74 3A 20
      00                         DB      0
‡
```

```
FCDE 53 54 45 50 20    STRMSG  DB      "STEP 5 - Push START to begin treament."
     35 20 2D 20 50
     75 73 68 20 53
     54 41 52 54 20
     74 6F 20 62 65
     67 69 6E 20 74
     72 65 61 74 6D
     65 6E 74 2E
     00                        DB      0
*
FD06 45 52 52 4F 52    EMSG_F  DB      "ERROR - Invalid FREQUENCY; Push CLEAR"
     20 2D 20 49 6E
     76 61 6C 69 64
     20 46 52 45 51
     55 45 4E 43 59
     3B 20 50 75 73
     68 20 43 4C 45
     41 52
     00                        DB      00
*
FD2C 54 72 65 61 74    FINMSG  DB      "Treatment Complete - Push Clear"
     6D 65 6E 74 20
     43 6F 6D 70 6C
     65 74 65 20 2D
     50 75 73 68 20
     43 6C 65 61 72
     00                        DB      00
*
FD4B 54 72 65 61 74    TLEVEL  DB      "Treatment Percentage: 000%"
     6D 65 6E 74 20
     50 65 72 63 65
     6E 74 61 67 65
     3A 20 30 30 30
     25
     00                        DB      00
*
FD66 75 41 4D 50 20    EMSG_%  DB      "uAMP Level Exceeded - Push Clear"
     4C 65 76 65 6C
     20 45 78 63 65
     65 64 65 64 20
     20 50 75 73 68
     20 43 6C 65 61
     72
     00
*
FD85
*
*       TABLES
*
        ORG     FE92
*
FE92            ASCTBL  DB      E2,30,D1,37,D2,38,D4,39,B1,34,B2,35
                        DB      B4,36,71,31,72,32,74,33,0
*
*       INPUT TEMPLATES
*
*       L , DP , VDP , SZ , XX , XX , XX , XX , 00 , # , VV , VV , VV , VV
```

```
*
*       L   = LENGTH OF INPUT BUFFER (CHAR CNT +1)
*       DP  = LAST DISPLAY POSITION OF INPUT FIELD
*       VDP = DISPLAY POSITION FOR VALID INPUT DATA (1st DISPLAY ROW)
*       SZ  = INPUT FIELD TEMPLATE SIZE (# OF BYTES)
*       XX  = THE INPUT FIELD TEMPLATE
*       #   = NUMBER OF VALID ENTRIES (EACH ENTRY IS 2 BYTES)
*       VV  = THE VALID ENRTIES
*
FEA7           I-TBUF   DB    05,66,19,05,20,20,3A,20,20,00,02,00,10,1F,F0
FEB6           I-FBUF   DB    04,65,10,04,20,20,2E,20,00,02,00,01,01,FF
FEC4           I-EBUF   DB    03,60,02,02,20,20,00,03,00,40,00,50,00,60
FED2           I-ABUF   DB    04,67,08,03,20,20,20,00,0E,00,20,00,30,00,40,00,50,00,60
                        DB    00,70,00,80,00,90,01,00,02,00,03,00,04,00,05,00,06,00
*
*
FEF7           VTBL_M   DB    40,F0,00,F2,67,50,F3,00,F6,00,60,F6,00,F9,99
*                                      |              |
*                                      I-START ADRS   |
*                                                     I- END ADRS
*
FF06           FRQTBL   DB    00,01,5A,00,02,50,00,03,46,00,04,3C,00,05,32,00,06,28,00,07,1E,00,08,
                              14,00,09
               END_F    DB    0A
*
FF21           VTBL_S   DB    40,XX,XX,YY,YY,50,XX,XX,YY,YY,60,XX,XX,YY,YY
*
FF30           IO_TBL   DB    00,20,03,FF,00,30,04,FF,00,40,05,FF,00,50,06,FF
                        DB    00,60,08,FF,00,70,09,FF,00,80,0A,FF,00,90,0B,FF
                        DB    01,00,0D,FF,02,00,1A,FF,03,00,26,FF,04,00,33,FF
                        DB    05,00,40,FF,06,00,4D,FF
*
FF68
*
*       SUBROUTINES
*
        ORG    E000
*
*       DELAY1: GENERATES A 122.98 uSEC DELAY.
*               ON ENTRY: NONE
*               ON EXIT : NONE
*
E000  36       DELAY1   PSHA                    * -4- SAVE CONTENTS
      86 18             LDAA    # 18            * -2-
      4A       DEL1     DECA                    * -1-
      26 FD             BNE     DEL1            * -3- LOOP UNTIL COUNT = 0
      32                PULA                    * -3- RESTORE CONTENTS
      39                RTS                     * -5-
*
*       DELAY2: GENERATES A 20 mSEC DELAY.
*               ON ENTRY: NONE
*               ON EXIT : NONE
*
E008  3C       DELAY2   PSHX                    * SAVE CONTENTS
      CE 01 00          LDX     # 100
      8D F2    DEL2     BSR     DELAY1
      09                DEX
```

```
        26 FB              BNE     DEL2            * LOOP UNTIL COUNT = 0
        38                 PULX
        39                 RTS
*
*       KEYSCN: CHECKS TO SEE IF A KEY IS PRESSED. IF SO, A 20 mSEC
*               DEBOUNCE IS USED TO VERIFY KEYCODE.
*               ON ENTRY: NONE
*               ON EXIT : ACCA =0; NO KEY PRESSED
*                         ACCA ()0; CONTAINS KEYCODE
*                         ACCB DESTROYED
*
E013 86 70      KEYSCN  LDAA    # 70            * SET SCANLINE 7 ACTIVE ( LOW )
     97 02      KEY1    STAA    PORT1D
     D6 02              LDAB    PORT1D          * IF KEY PRESSED SCANLINE 0-3 ACTIVE
     CA F0              ORAB    # F0            * MASK SCANLINE
     53                 COMB                    * KEY NOW ACTIVE HIGH
     26 0B              BNE     KEY3            * ANY KEY PRESSED?
     0D                 SEC
     46                 RORA                    * NO, SHIFT TO NEXT SCANLINE
     81 F7              CMPA    # F7            *     FINISHED LAST ONE?
     26 F1              BNE     KEY1
     7A 00 80           CLR     KEYHLD          * YES, CLR FLAG TO INDICATE
     4F         KEY2    CLRA                    *     THAT A KEY THAT WAS
     39                 RTS                     *     PRESSED IS RELEASED
     7D 00 80   KEY3    TST     KEYHLD          * MAKE SURE LAST KEY HAS BEEN
     26 F9              BNE     KEY2            * RELEASED
     84 F0      KEY3    ANDA    # F0            * IF SO,
     97 80              STAA    KEYHLD          * SAVE DETECTED SCANLINE
     8D D4              BSR     DELAY2
     96 02              LDAA    PORT1D          * GET KEY PRESSED AGAIN
     8A F0              ORAA    # F0            * MASK SCANLINE
     43                 COMA                    * KEY NOW ACTIVE HIGH
     11                 CBA                     * SAME KEY STILL PUSHED?
     26 EB              BNE     KEY2            * NO, RETURN
     9A 80              ORAA    KEYHLD          * ADD SCANLINE TO MAKE UNIQUE KEYCODE
     39                 RTS
*
*    CSRLFT - SET DISPLAY CURSOR MOVE DIRECTION TO LEFT.
*    CSRRHT - SET DISPLAY CURSOR MOVE DIRECTION TO RIGHT.
*             ON ENTRY: NONE
*             ON EXIT : NONE
*                       ACCA DESTROYED
*
E03F 86 04      CSRLFT  LDAA    # 4             * DIR = LEFT
     20 02              BRA     CSR1
E043 86 06      CSRRHT  LDAA    # 6             * DIR = RIGHT
     B7 60 01   CSR1    STAA    DISPC           * SET SELECTED DIRECTION
     8D B6              BSR     DELAY1
     39                 RTS
*
*    FILBUF - ACCEPTS KEYBOARD ENTRIES UNTIL ENTER IS PRESSED THEN
*             VERIFIES THEM AGAINST THE TABLE POINTED TO BY XREG.
*             ENTRY: XREG - POINTER TO VALID KEYIN TABLE
*                    TEMP2 - LOC -1 POINTER
*                    BUFPTR - LOC POINTER
*             EXIT : C = 1; ERROR - NO VALID CODE
*                    C = 0; ACCA - CONTAINS KEYIN CODE
```

```
*                       ALL REGISTERS DESTROYED
*
E04B DF 85    FILBUF   STX    TEMPLT       * SAVE POINTER TO INPUT TEMPLATE
     A6 00             LDAA   0,X
     97 82             STAA   CHARCT       * MAX CHARACTER COUNT
     C6 03             LDAB   # 3
     3A                ABX                 * MOVE PAST DISPLAY CSR POSITION
     E6 00             LDAB   0,X          * HOLD DISPLAY TEMPLATE SIZE
     08                INX                 * POINT TO DISPLAY TEMPLATE
     DF 89             STX    TEMP2A
     BD E1 CE          JSR    OUTSTR       * OUTPUT DISPLAY TEMPLATE
     CE 00 90          LDX    # INBUF
     DF 87             STX    BUFPTR       * SAVE POINTER TO INPUT BUFFER
*
*        MOVE REVERSE COPY OF TEMPLATE TO INPUT BUFFER
*
     3A                ABX                 * POINT TO END OF INPUT BUFFER
     4F                CLRA
     A7 00             STAA   0,X          * MARK END OF INPUT BUFFER
     DF 83    FILINB   STX    TEMP2        * SAVE INPUT BUFFER POINTER
     DE 89             LDX    TEMP2A       * GET POINTER TO DISPLAY TEMPLATE
     A6 00             LDAA   0,X          * GET TEMPLATE CHARACTER
     27 0A             BEQ    FIL0
     08                INX
     DF 89             STX    TEMP2A       * SAVE DISPLAY TEMPLATE POINTER
     DE 83             LDX    TEMP2        * GET INPUT BUFFER POINTER
     09                DEX
     A7 00             STAA   0,X          * TEMPLATE CHAR -) INPUT BUFFER
     20 EE             BRA    FILINB
     8D C6    FIL0     BSR    CSRLFT       * SET CURSOR DIRECTION = LEFT
E079 8D 98    FIL1     BSR    KEYSCN       * LOOP UNTIL KEY PRESSED
     4D                TSTA
     27 FB             BEQ    FIL1
     81 E8             CMPA   # ENTERC     * IS IT THE ENTER CODE?
     27 65             BEQ    FIL4
     81 E1             CMPA   # CLEARC     * NO, IS IT THE CLEAR ENTRY CODE?
     27 4E             BEQ    FIL3
     BD E0 F6          JSR    ASCII#       * NO, CONVERT KEY TO ASCII NUMBER
     25 EE             BCS    FIL1         * IF NOT ASCII NUMBER GET ANOTHER KEY
     7A 00 82          DEC    CHARCT
     2F 60             BLE    FIL5         * NO, CHARACTER COUNT = 0?
     C6 20             LDAB   # 20         * ACCB = SPACE CHAR
     DE 87             LDX    BUFPTR
     8C 00 90          CPX    # INBUF      * POINTING TO 1ST LOCATION IN BUFFER?
     26 14             BNE    F1
     A7 00             STAA   0,X          * YES, PUT CHAR IN BUFFER
     DF 83             STX    TEMP2        * AND SAVE LOCATION
     08       F2       INX
     6D 00             TST    0,X          * CONTENTS = 0 (END OF BUFFER)?
     27 04             BEQ    F6
     E1 00             CMPB   0,X          * NO, IS NEXT LOCATION = SPACE?
     26 F7             BNE    F2
     DF 87    F6       STX    BUFPTR       * YES, SAVE NEXT LOC POINTER
     BD E1 DF          JSR    OUTBUF       * NO, DISPLAY CHARACTER
     20 CC             BRA    FIL1         * AND GET MORE INPUT
*
*        IF 1ST CHAR LOC NOT EMPTY MOVE ALL CHAR'S RIGHT 1 LOC
```

```
E8AD  3C        F1    PSHX                  * SAVE BUFFER POINTER
      36              PSHA                  * SAVE NEW CHAR
      DE 83           LDX    TEMP2          * GET LOC-1 POINTER
      A6 00           LDAA   0,X
      DE 87     F4    LDX    BUFPTR         * GET LOC POINTER
      A7 00           STAA   0,X            * MOVE CHAR RIGHT 1 PLACE
      DE 83           LDX    TEMP2
      DF 87           STX    BUFPTR         * SET LOC = LOC -1
      8C 00 90  F3    CPX    # INBUF        * IS LOC -1 FIRST LOC IN BUFFER?
      27 0C           BEQ    F5
      09              DEX
      A6 00           LDAA   0,X            * GET LOC -1 CHAR
      BD E1 7D        JSR    DIGIT?         * IS CHAR A NUMBER?
      25 F3           BCS    F3
      DF 83           STX    TEMP2          * YES, THEN SAVE AS NEW LOC-1
      20 E7           BRA    F4

*
*       WHEN ALL CHAR'S ARE MOVED 1 PLACE RIGHT
*
E8CC  32        F5    PULA                  * GET NEW CHAR BACK
      A7 00           STAA   0,X            * PUT AT 1ST LOC IN BUFFER
      38              PULX                  * RESTORE ORIG LOC POINTER
      DF 83           STX    TEMP2          * AS LOC-1 POINTER AND
      20 C6           BRA    F2             * MOVE LOC POINTER 1 SPACE RIGHT
*
*       IF CLEAR KEY PRESSED
*
E8D4  DE 85     FIL3  LDX    TEMPLT
      A6 01           LDAA   1,X            * GET DISPLAY CURSOR POSITION
      A0 03           SUBA   3,X            * POINT TO START OF DISPLAY FIELD
      4C              INCA
      BD E1 B0        JSR    SETCSR
      BD E0 00        JSR    DELAY1
      BD E0 43        JSR    CSRRHT         * CURSOR DIRECTION = RIGHT
      7E E0 4B        JMP    FILBUF         * START OPERATION OVER
*
*       IF ENTER KEY PRESSED
*
E8E7  DE 85     FIL4  LDX    TEMPLT         * GET POINTER TO VALID DATA
      8C FE B6        CPX    # I-FBUF       * IS IT THE FREQUENCY OR TIME ENTRY?
      23 1B           BLS    VDATAA
      20 31           BRA    VDATAB         * NO, THEN MUST BE EMF OR AMP ENTRY
      BD E1 89  FIL5  JSR    BEEP           * ENTERED TO MANY CHARACTERS
      7E E0 79        JMP    FIL1           * WAIT FOR ENTER OR CLEAR KEY
*
*       ASCII# - CHANGES KEYIN TO AN ASCII NUMBER IF POSSIBLE.
*               ON ENTRY: ACCA = KEYIN TO CONVERT
*               ON EXIT : C = 1 ; CONVERSION FAILED
*                         C = 0 ; CONVERSION SUCCESSFUL
*                            ACCA = ASCII KEY CODE
*                         XREG DESTROYED
*
E8F6  CE FE 92  ASCII# LDX   # ASCTBL       * POINT TO TABLE OF ASCII #'S
      A1 00     ASC2  CMPA   0,X            * KEYIN MATCH TABLE ENTRY?
      27 08           BEQ    ASC1
      08              INX                   * NO GO TO NEXT ENTRY
```

```
        08              INX
        6D 00           TST     0,X             * END OF TABLE?
        26 F6           BNE     ASC2
        0D              SEC                     * YES, SET FAIL FLAG
        39              RTS
        A6 01   ASC1    LDAA    1,X             * ASCII NUMBER -> ACCA
        0C              CLC                     * CLEAR FAIL FLAG
        39              RTS

*
*       VDATAA - CONVERTS INPUT BUFFER TO NUMBER AND CHECKS IF
*                IN RANGE.
*                ON ENTRY: XREG POINTS TO TEMPLATE
*                ON EXIT : C = 1 ; ERROR
*                          C = 0 ; ACCD = INPUT NUMBER
*
E109 8D 37   VDATAA BSR     MAKE#           * CONVERT INPUT DATA TO NUMBER
     E6 00           LDAB    0,X             * NUMBER IN TEMP2
     3A              ABX
     C6 06           LDAB    # 6
     3A              ABX                     * POINT TO LOWER LIMIT
     DC 83           LDD     TEMP2           * GET INPUT DATA NUMBER
     A3 00           SUBD    0,X             * SUBTRACT LOWER LIMIT
     2B 08           BMI     VDATA5          * IF RESULT - ; ERROR
     A3 02           SUBD    2,X             * SUBTRACT (U LIMIT- L LIMIT)
     22 04           BHI     VDATA5          * IF RESULT NOT - ; ERROR
     0C              CLC                     * RESULT OK
     DC 83           LDD     TEMP2           * GET INPUT NUMBER
     39              RTS
     0D      VDATA5  SEC                     * RESULT BAD
     39              RTS

*
*       VDATAB - CONVERTS INPUT BUFFER TO NUMBER AND CHECKS IN
*                LIST OF VALID ENTRIES.
*                ON ENTRY: XREG POINTS TO TEMPLATE
*                ON EXIT : C = 1 ; ERROR
*                          C = 0 ; VALID, SELECTION # IN ACCD REVERSED
*
E121 8D 1F   VDATAB  BSR     MAKE#           * CONVERT INPUT DATA TO NUMBER
     E6 00           LDAB    0,X             * NUMBER IN TEMP2
     3A              ABX
     C6 04           LDAB    # 4
     3A              ABX                     * POINT TO # OF VALID ENTRIES
     E6 00           LDAB    0,X
     D7 81           STAB    TEMP1           * COUNT -> TEMP1
     DC 83   VDATA1  LDD     TEMP2           * GET INPUT NUMBER
     08              INX
     A3 00           SUBD    0,X             * INPUT = VALID SELECTION?
     27 08           BEQ     VDATA2
     7A 00 81        DEC     TEMP1           * NO, END OF VALID ENTRIES LIST?
     27 07           BEQ     VDATA3
     08              INX                     * NO, BUMP TO NEXT ENTRY
     20 F1           BRA     VDATA1
     0C      VDATA2  CLC                     * FOUND MATCH
     DC 83           LDD     TEMP2
     39              RTS
     0D      VDATA3  SEC                     * NO MATCH; ERROR OUT
     39              RTS
```

```
*
*
*       MAKE# - CONVERTS NUMBERS IN BUFFER TO A BCD VALUE.
*              ON ENTRY: NONE
*              ON EXIT : TEMP2 = BCD VALUE
*
E142 3C        MAKE#   PSHX                    * SAVE TEMPLATE POINTER
     86 04             LDAA    #4
     97 82             STAA    CHARCT          * INITIALIZE CHAR COUNT
     CE 00 90          LDX     # INBUF         * POINT TO NUMBER TO CONVERT
     A6 00   MAKE1     LDAA    0,X             * GET A DIGIT
     27 1C             BEQ     MAKE3           * IF =0 DONE
     8D                BSR     DIGIT?
     25 15             BCS     MAKE2           * IS IT A DIGIT?
     48                ASLA                    * YES, SHIFT BCD DIGIT
     48                ASLA                    *     TO UPPER NYBBLE
     48                ASLA
     48                ASLA
     36                PSHA
     DC 83             LDD     TEMP2
     04                LSRD                    * CLR UPPER NYBBLE
     04                LSRD
     04                LSRD
     04                LSRD
     DD 83             STD     TEMP2
     32                PULA
     9A 84             ORAA    TEMP2 +1        * PUT IN DIGIT UPPER NYBBLE
     97 84             STAA    TEMP2 +1
     7A 00 82          DEC     CHARCT
     08      MAKE2     INX                     * GET NEXT DIGIT FROM DISPLAY
     20 E0             BRA     MAKE1
     86 04             LDAA    # 4
     D6 82             LDAB    CHARCT          * FIND # OF SHIFTS NEEDED TO
     3D                MUL                     * ALIGN BCD INPUT VALUE
     1B                XGDX
     DC 83   MAKE3     LDD     TEMP2           * GET NUMBER
     08                INX                     * SET/CLR Z-FLAG
     09      MAKE5     DEX
     27 03             BEQ     MAKE4
     04                LSRD
     20 FA             BRA     MAKE5
     DD 83             STD     TEMP2           * SAVE FINAL RESULT
     38                PULX                    * RESTORE TEMPLATE POINTER
     39                RTS
*
*       DIGIT? - CHECKS TO SEE IF ACCA IS WITHIN AN ASCII 0-9.
*              ON ENTRY: ACCA = NUMBER TO BE TESTED
*              ON EXIT : C = 1 ; FAILED
*                        C = 0 ; ITS AN ASCII DIGIT
*
E17D 81 2F    DIGIT?    CMPA    # 2F           * ACCA ( ASCII 0?
     23 06              BLS     DIGIT1
     81 39              CMPA    # 39           * ACCA ) ASCII 9?
     22 02              BHI     DIGIT1
     0C                 CLC                    * NO, ITS AN ASCII DIGIT
     39                 RTS
```

```
                00      DIGIT1  SEC                     * YES, ITS NOT AN ASCII DIGIT
                39              RTS
*
*       BEEP - SOUNDS THE ERROR BEEPER.
*               ON ENTRY: NONE
*               ON EXIT : ACCA DESTROYED
*
E189 86 08      BEEP    LDAA    # 8             * SELECT TONE # 1
     20 06              BRA     BEEP3
     86 04      BEEP1   LDAA    # 4             * SELECT TONE # 2
     20 02              BRA     BEEP3
     86 0C      BEEP2   LDAA    # C             * SELECT TONE # 3
     97 03      BEEP3   STAA    PORT4D          * TURN ON BEEP
     86 0A              LDAA    # 0A            * FOR .5 SEC
     BD E0 08   BEEP4   JSR     DELAY2
     4A                 DECA
     26 FA              BNE     BEEP4
     97 03              STAA    PORT4D          * TURN OFF BEEP
     39                 RTS
*
*
E1A0 01                 NOP                     * HOLD ROOM FOR PATCHS
     01                 NOP
     01                 NOP
     01                 NOP
     01                 NOP
     01                 NOP
     01                 NOP
     01                 NOP
     01                 NOP
     01                 NOP
     01                 NOP
     01                 NOP
     01                 NOP
     01                 NOP
     01                 NOP
E1AF 01                 NOP
*
*
*       SETCSR: SETS CURSOR TO THE SELECTED ROW/COLUMN ON DISPLAY
*               ON ENTRY: ACCA BIT6 = ROW SELECT; 0-ROW 0 : 1-ROW 1
*                         ACCA BIT5-0 = COLUMN SELECT; 0 TO 39
*                         ACCA DESTROYED
*
E1B0 8A 80      SETCSR  ORAA    # 80            * SET MOVE CURSOR CONTROL BIT
     B7 60 01           STAA    DISPC
     39                 RTS
*
*       OUT2RW: OUTPUT THE STRING POINTED TO BY XREG AT THE FIRST
*               CHARACTER POSITION OF THE SECOND ROW OF THE DISPLAY.
*               ON ENTRY: XREG = ADDRESS OF MESSAGE
*               ON EXIT : XREG, ACCB, ACCA DESTROYED
*
*       OUTSTR: OUTPUT THE STRING POINTED TO BY THE XREG AT CURRENT
*               DISPLAY POSITION.
*
E1B6 86 40      OUT2RW  LDAA    # 40            * ADDRESS OF SECOND ROW
```

```
        8D F6              BSR     SETCSR
        BD E0 00           JSR     DELAY1
        86 20              LDAA    # 20
        C6 28              LDAB    # 28                 * BLANK 2ND LINE OF DISPLAY
        8D 15    OUT1      BSR     OUTCHR
        01                 NOP                          * CAN BE REMOVED!!
        5A                 DECB
        26 FA              BNE     OUT1
        86 40              LDAA    # 40                 * PUT CURSOR TO START OF 2ND ROW
E1C9    8D E5    COUTS     BSR     SETCSR
E1CB    BD E0 00 WOUTS     JSR     DELAY1
E1CE    A6 00    OUTSTR    LDAA    0,X                  * GET CHARACTER OF MESSAGE
        27 05              BEQ     OUT2                 * IS IT THE TERMINATOR CHARACTER?
        8D 04              BSR     OUTCHR               * NO, OUTPUT CHARACTER
        08                 INX
        20 F7              BRA     OUTSTR               * LOOP FOR NEXT CHARACTER
        39       OUT2      RTS
E1D8    B7 60 00 OUTCHR    STAA    DISPD                * OUTPUT CHAR IN ACCA
        BD E0 00           JSR     DELAY1
        39                 RTS
*
*       OUTBUF: OUTPUT THE CONTENTS OF THE INPUT BUFFER TO THE DISPLAY.
*               ON ENTRY: TEMPLT = THE CURRENT TEMPLATE ADDRESS
*               ON EXIT:  ACCA, XREG DESTROYED
*
E1DF    DE 85    OUTBUF    LDX     TEMPLT               * GET CURSOR LOCATION
        A6 01              LDAA    1,X
        8D CB              BSR     SETCSR
        CE 00 90           LDX     # INBUF              * GET LOCATION OF DATA TO OUTPUT
        8D E1              BSR     WOUTS
        39                 RTS
*
*       OUTDAC: OUTPUT NUMBER IN ACCD TO DAC.
*               ON ENTRY: ACCD = VALUE TO OUTPUT
*               ON EXIT : ACCA DESTROYED
*
E1EB    B7 80 00 OUTDAC    STAA    PORT2D               * OUTPUT MS 2 BITS OF DATA
        F7 80 02           STAB    PORT3D               * OUTPUT LS BYTE OF DATA
        B6 80 03           LDAA    PORT3C
        84 F7              ANDA    # F7                 * SET DAC STROBE
        B7 80 03           STAA    PORT3C
        8A 08              ORAA    # 08                 * CLEAR DAC STROBE
        B7 80 03           STAA    PORT3C
        39                 RTS
*
*       SYSTEM INITIALIZATION ROUTINE
*               ON POWER UP INITIALIZE ALL SYSTEM COMPONETS.
*
E1FF    8E 00 FF START     LDS     # FF                 * SETUP THE STACK POINTER
*
*       INITIALIZE KEYBOARD PORT
*
E202    86 F0              LDAA    # F0
        97 00              STAA    PORT1C               * SET BITS 7-4 OUTPUT; 3-0 INPUT
        97 02              STAA    PORT1D               * ALL DRIVERS (7-4) INACTIVE
*
```

```
*       INITIALIZE BEEPER PORT
*
E208  86 18           LDAA    # 18
      97 01           STAA    PORT4C        * BITS 3,4 OUTPUT ON PORT 4
*
*       INITIALIZE DISPLAY
*
E20C  86 38           LDAA    # 38          * INITIALIZE DISPLAY
      B7 60 01        STAA    DISPC         * SET DISPLAY FUNCTION (8 BITS/2 LINES)
      BD E0 00        JSR     DELAY1
      86 0C           LDAA    # 0C          * SET DISPLAY ON
      B7 60 01        STAA    DISPC
      BD E0 00        JSR     DELAY1
      BD E0 43        JSR     CSRRHT        * CURSOR MOVE DIRECTION = RIGHT
*
*       INITIALIZE DAC ( PORTS 2 & 3)
*
E21F  86 FF           LDAA    # FF          * TO DATA DIR REG MAKES-
      CE 80 00        LDX     # PORT2D
      A7 00           STAA    0,X           * PORT 2 LINES ALL OUTPUTS.
      A7 02           STAA    2,X           * PORT 3 LINES ALL OUTPUTS
      86 04           LDAA    # 4
      A7 01           STAA    1,X           * SELECT DATA PORT A
      86 3C           LDAA    # 3C
      A7 03           STAA    3,X           * SELECT DATA PORT B,
      CC 02 00        LDD     # 200         * CB2 IS OUTPUT AND FOLLOWS BIT3
      8D B6           BSR     OUTDAC        * SET DAC OUTPUT TO ZERO VOLTS
*
*       OUTPUT WAVEFORM AND POLARITY DISPLAYS
*
E235  7F 00 8B  IDISPL CLR    POLS          * SET STATUS FOR BI-PHASIC DISPLAY
      86 24           LDAA    # 24          * SET CURSOR TO LOCATION 36
      BD E1 B0        JSR     SETCSR
      CE FC 00        LDX     BI_FAZ        * POINTER TO "+/-" STRING
      BD E1 CB        JSR     WOUTS
      7F 00 8C        CLR     WFORMS        * SET STATUS FOR MODIFED SQUARE WAVEFORM
      86 1F           LDAA    # 1F          * SET CURSOR TO LOCATION 31
      BD E1 B0        JSR     SETCSR
      BD E0 00        JSR     DELAY1
      86 4D           LDAA    # 'M
      BD E1 D8        JSR     OUTCHR        * OUTPUT DISPLAY INDICATOR
*
* ---------------- MAIN PROGRAM ----------------
*
*       REQUESTS TREATMENT PARAMETERS AND VERIFIES ALL SELECTIONS.
*
E253  CE FC 52  REQEMF LDX    # VMSG        * REQUEST TREATMENT VOLTAGE
      BD E1 B6        JSR     OUT2RW
      CE FE C4        LDX     # I-EBUF      * EMF INPUT TEMPLATE
      BD E0 4B        JSR     FILBUF
      24 08           BCC     REQV1         * IF ILLEGAL;
      BD E1 89        JSR     BEEP          * BEEP USER & RETRY
      BD E0 43        JSR     CSRRHT
      20 EA           BRA     REQEMF
      DD A0    REQV1  STD     VOLTS         * ELSE SAVE USER INPUT
      CE FE C4        LDX     # I-EBUF
      A6 02           LDAA    2,X           * GET VALID DATA DISPLAY LOC
```

```
       CE 00 90              LDX      # INBUF
       BD E1 C9              JSR      COUTS           * DISPLAY EMF INPUT
       BD E0 43              JSR      CSRRHT
       CE FC 72    REQAMP    LDX      # AMPMSG        * REQUEST TREATMENT AMPERAGE
       BD E1 B6              JSR      OUT2RW
       CE FE D2              LDX      # I-ABUF        * uAMP INPUT TEMPLATE
       BD E0 4B              JSR      FILBUF
       24 05                 BCC      REQA1           * IF ILLEGAL;
       BD E1 89              JSR      BEEP            * BEEP USER & RETRY
       20 EA                 BRA      REQAMP
       DD A2      REQA1      STD      AMPS            * ELSE SAVE USER INPUT
       CE FE D2              LDX      # I-ABUF
       A6 02                 LDAA     2,X             * GET VALID DATA DISPLAY LOC
       CE 00 90              LDX      # INBUF
       BD E1 C9              JSR      COUTS           * DISPLAY uAMP INPUT
       BD E0 43              JSR      CSRRHT
       CE FC 98   REQFRQ     LDX      # FRQMSG        * REQUEST TREATMENT FREQUENCY
       BD E1 B6              JSR      OUT2RW
       CE FE B6              LDX      # I-FBUF        * FREQUENCY INPUT TEMPLATE
       BD E0 4B              JSR      FILBUF
       24 05                 BCC      REQF1           * IF INPUT ILLEGAL;
       BD E1 89              JSR      BEEP            * BEEP USER & RETRY
       20 EA                 BRA      REQFRQ
       DD A4                 STD      HERTZ           * SAVE VALID INPUT
       CE FE B6              LDX      # I-FBUF
       A6 02                 LDAA     2,X             * GET VALID DATA DISPLAY LOC
       CE 00 90              LDX      # INBUF
       BD E1 C9              JSR      COUTS           * OUTPUT SELECTED HERTZ
       BD E0 43              JSR      CSRRHT
       CE FC BB   REQTIM     LDX      # TIMMSG        * REQUEST TREATMENT TIME
       BD E1 B6              JSR      OUT2RW
       CE FE A7              LDX      # I-TBUF
       BD E0 4B              JSR      FILBUF
       24 05                 BCC      REQT1           * IF INPUT ILLEGAL;
       BD E1 89              JSR      BEEP            * BEEP USER & RETRY
       20 EA                 BRA      REQTIM
       DD A6      REQT1      STD      TIME            * SAVE VALID INPUT
       CE FE A7              LDX      # I-TBUF
       A6 02                 LDAA     2,X             * GET VALID DATA DISPLAY LOC
       CE 00 90              LDX      # INBUF
       BD E1 C9              JSR      COUTS
       BD E0 43              JSR      CSRRHT
       CE FC DE              LDX      # STRMSG        * OUTPUT START MESSAGE
       BD E1 B6              JSR      OUT2RW
*
*     WAIT FOR START OR OTHER BUTTONS TO BE PUSHED
*
E2E8   BD E0 13   MAIN1      JSR      KEYSCN
       4D                    TSTA
       27 FA                 BEQ      MAIN1           * WAIT FOR KEYIN
       81 78                 CMPA     # STARTC        * IS IT A START KEYIN?
       27 4A                 BEQ      WAVEFM
       81 E1                 CMPA     # CLEARC        * NO, IS IT A CLEAR KEYIN?
       26 0B                 BNE      MAIN1A
       86 01                 LDAA     # 1             * YES, CLEAR DISPLAY
       B7 60 01              STAA     DISPC
       BD E0 08              JSR      DELAY2
```

```
*
*       POLARITY CODE DEFINITIONS
*               VARIABLE: POLS
*                               00 = BI-PHASIC WAVEFORM
*                               01 = POSITIVE WAVEFORM
*                               02 = NEGATIVE WAVEFORM
*
     7E E2 35          JMP      IDISPL      * AND REQUEST ALL PARAMETERS OVER
     81 B8     MAIN1A  CMPA     # POLC      * IS IT THE POLARITY TOGGLE KEY?
     26 18             BNE      MAIN1C
     D6 8B             LDAB     POLS        * YES, GET CURRENT DISPLAY FLAG
     5C                INCB                 * CHANGE TO NEXT FLAG
     C1 03             CMPB     # 03
     26 01             BNE      MAIN1B
     5F                CLRB
     D7 8B     MAIN1B  STAB     POLS        * SAVE FLAG
     86 04             LDAA     # 04        * COMPUTE ADRS OF STRING TO CHANGE DISPLAY TO
     3D                MUL
     CE FC 00          LDX      # BI_FAZ    * BASE ADRS
     3A                ABX                  *          + OFFSET
     86 24             LDAA     # 24        * CURSOR DISPLAY LOCATION
     BD E1 C9          JSR      COUTS       * SET CURSOR & OUTPUT STRING
     20 CB             BRA      MAIN1
*
*       WAVE SHAPE CODE DEFINITIONS
*               VARIABLE: WAVES
*                               00 = MODIFIED SQUARE WAVEFORM
*                               FF = SQUARE WAVEFORM
*
E31D 81 D8     MAIN1C  CMPA     # WFORMC    * IS IT THE WAVEFORM TOGGLE KEY?
     26 C7             BNE      MAIN1
     86 1F             LDAA     # 1F        * CURSOR DISPLAY LOCATION
     BD E1 B0          JSR      SETCSR
     BD E0 00          JSR      DELAY1
     D6 8C             LDAB     WFORMS      * YES, GET THE WAVEFORM DISPLAY STATUS
     27 05             BEQ      MAIN1D
     5C                INCB                 * TOGGLE WAVEFORM FLAG
     86 4D             LDAA     # ' M       * TO MODIFIED SQUARE
     20 03             BRA      MAIN1E
     5A        MAIN1D  DECB                 * TOGGLE WAVEFORM FLAG
     86 53             LDAA     # ' S       * TO SQUARE
     D7 8C     MAIN1E  STAB     WFORMS      * SAVE FLAG
     BD E1 D8          JSR      OUTCHR      * AND CHANGE DISPLAY
     20 AC             BRA      MAIN1
*
*       ALL ENTERED DATA IS VALID AND THE START KEY HAS BEEN
*       PUSHED, SELECT FREQUENCY MULTIPLIER.
*
E33C CE FF 06  WAVEFM  LDX      # FRQTBL    * POINTER TO GET CORRECT FREQUENCY MULTIPLIER
     EC 00     MAIN2   LDD      0,X         * GET TRIAL FREQUENCY
     93 A4             SUBD     HERTZ       * SUBTRACT USER SELECTED FREQUENCY
     27 1B             BEQ      MAIN4
     08                INX                  * DIDN'T MATCH TRY NEXT VALUE
     08                INX
     08                INX
     8C FF 21          CPX      END_F       * END OF .1 - .9 FREQUENCY TABLE?
```

```
         26 F2                  BNE     MAIN2
         CE FD 06               LDX     # EMSG_F         * IF NOT FOUND INDICATE ERROR
         BD E1 B6               JSR     OUT2RW
         BD E1 89               JSR     BEEP
         BD E0 13    MAIN3      JSR     KEYSCN           * WAIT FOR USER RESPONSE
         81 E1                  CMPA    # CLEARC
         26 F9                  BNE     MAIN3
E35D  7E E2 9C                  JMP     REQFRQ           * THEN GO REQUEST FREQUENCY
*
*
E360  A6 02         MAIN4      LDAA    2,X              * GET FREQUENCY MULTIPLIER
      97 80                     STAA    FQ_MUL
*
*
*
E364  7D 00 8C                  TST     WFORMS           * SELECT MODIFIED OR
      27 05                     BEQ     MAIN5            * SQUARE WAVEFORM VOLTAGE
      CE FF 21                  LDX     # VTBL_S         * TABLE
      20 03                     BRA     MAIN6
*
*      SEARCH VOLTAGE TABLE FOR START AND END OF VOLTAGE DELAY
*      VALUES FOR THIS SELECTION.
*
E36E  CE FE F7      MAIN5      LDX     # VTBL_M         * POINTER TO TABLE OF VALID VOLTAGES
      A6 00         MAIN6      LDAA    0,X              * GET TRIAL VOLTAGE
      90 A1                    SUBA    VOLTS +1         * SUBTRACT USER SELECTED VOLTAGE
      27 07                    BEQ     MAIN7
      08                       INX                      * DIDN'T MATCH TRY NEXT VALUE
      08                       INX
      08                       INX
      08                       INX
      08                       INX
      20 F3                    BRA     MAIN6
      EC 03         MAIN7      LDD     3,X              * FOUND MATCH; GET ENDING ADRS OF VOLTAGE TABLE
      DD 87                    STD     TBLEND           * AND SAVE A COPY
      EC 01                    LDD     1,X              * AND GET STARTING ADRS OF TABLE
      DD 85                    STD     V_TBL            * AND SAVE A COPY
E386  DD 96                    STD     XHOLD            * INTERRUPT ROUTINE POINTER
*
*      CHECK POLARITY TO SET EITHER POSITIVE OR NEGATIVE
*      WAVEFORM.
*
E388  96 8B                    LDAA    POLS             * SELECTED POLARITY = BI-PHASIC?
      27 09                    BEQ     MAIN8
      81 01                    CMPA    # 1              * NO, IS IT POSITIVE ONLY?
      27 05                    BEQ     MAIN8
      CC 00 01                 LDD     # 1              * NO, SET INCREMENT VALUE = 1 (NEGATIVE WAVEFORM START)
      20 03                    BRA     MAIN9
      CC FF FF      MAIN8      LDD     # FFFF           * SET INCREMENT VALUE = -1 (POSITIVE WAVEFORM START)
      DD 8D         MAIN9      STD     INCVAL
*
*      SET VARIABLE IOMAX TO THE MAXIMUM COUNT ALLOWED
*      ACCORDING TO THE MAX uAMPS, AS SELECTED BY THE
*      USER.
*
E39A  CE FF 30                 LDX     # IO_TBL         * POINTER TO THE uAMP COUNT CONVERSION TABLE
```

```
      EC 08     MAIN10  LDD    0,X         * GET TRIAL uAMP VALUE
      93 A2             SUBD   AMPS        * SUBTRACT USER SELECT uAMP VALUE
      27 06             BEQ    MAIN11
      08                INX                * NO MATCH, MOVE TO NEXT VALUE
      08                INX
      08                INX
      08                INX
      20 F4             BRA    MAIN10
      A6 02     MAIN11  LDAA   2,X         * GET Io MAX DIVISOR
      97 A9             STAA   IOMAX+1
      7F 00 A8          CLR    IOMAX
*
*        OUTPUT PERCENTAGE OF TREATMENT MESSAGE ON 2ND ROW
*        OF DISPLAY.
*
E380 CE FD 4B           LDX    # TLEVEL    * POINTER TO MESSAGE
     BD E1 B6            JSR    OUT2RW
     BD E0 3F            JSR    CSRLFT     * SET CURSOR MOVE DIR = LEFT
```

```
*
*
*
*      THIS IS THE CODE TO GENERATE THE .1 TO .9 HERTZ WAVEFORM
*
*    ---------------------------------------------------------------
*    - THE DATA TABLE ENTRY FORMAT IS AS FOLLOWS;                  -
*    -                                                             -
*    -     CC LL HH                                                -
*    -     |  |  |                                                 -
*    -     |  |  |-- HIGH ORDER DELAY BYTE                         -
*    -     |  |----- LOW ORDER DELAY BYTE                          -
*    -     |-------- LOOP REPEAT COUNT                             -
*    -                                                             -
*    - THE DATA TABLE IS BUILT FROM PROCESSED ENTRIES DERIVED FROM -
*    - THE .9 HERTZ WAVEFORM. THE PROCESS FOR DERIVING THE TABLE   -
*    - VALUES IS DESCRIBED BELOW;                                  -
*    -                                                             -
*    - WV (us) / 11.18 = TD                                        -
*    -                                                             -
*    - (TD / 728) + 1 = CC                                         -
*    -                     if CC = 1 : HH LL = TD                  -
*    -                     else      : HH LL = 728                 -
*    -                                                             -
*    - WHERE :   WV = .9 HERTZ WAVEFORM VALUE                      -
*    -           TD = TOTAL DELAY                                  -
*    -           11.18 = THE CLOCK TIME (us) * MINIMUM FREQ MUL    -
*    -           728   = THE MAXIMUM TIMER DELAY VALUE             -
*    -                                                             -
*    - THE .1 TO .9 HERTZ WAVEFORM GENERATION PROGRAM MULTIPLIES   -
*    - THE TABLE DELAY VALUE (HH LL) BY THE FREQUENCY MULTIPLIER   -
*    - WHICH GIVES A DELAY VALUE SCALED TO THE FREQUENCY. THIS     -
*    - VALUE IS USED BY THE 6303 TIMER TO GENERATE AN INTERRUPT    -
*    - AFTER A SPECIFIC TIME INTERVAL WHICH REPEATS CC TIMES. THIS -
*    - GENERATES THE REQUIRED DELAY BETWEEN CONSECUTIVE VOLTAGE    -
*    - OUTPUT VALUES.                                              -
*    -                                                             -
*    - THE FREQUENCY MULTIPLIER TABLE IS AS FOLLOWS;               -
```

```
*  -
*  -   FREQ (Hz)   MULTIPLIER      FREQ (Hz)   MULTIPLIER   -
*  -    .1            90              .2          80        -
*  -    .3            70              .4          60        -
*  -    .5            50              .6          40        -
*  -    .7            30              .8          20        -
*  -    .9            10                                    -
*  --------------------------------------------------------
*
*
*
E3B9  CC 02 00        LDD    # 200            * SET DACVAL = 0 VOLTS
      DD 89           STD    DACVAL
      7F 00 82        CLR    COUNT
      7F 00 8F        CLR    LASMAX           * SET LAST MAX io TO ZERO
      86 08           LDAA   # 08
      97 88           STAA   T_CTRL           * ENABLE TIMER INTERRUPTS
      86 3D           LDAA   # 3D             * ENABLE CLOCK INTERRUPTS
      B7 80 03        STAA   PROT3C
      0E              CLI                     * RELEASE PENDING INTERRUPTS
*
* ----------------------------------------------------------
*     THIS ROUTINE CHECKS THE ADC AND COMPUTES THE
*     PERCENTAGE OF TREATMENT, OUTPUTTING IT TO THE DISPLAY.
*
*     CNT = A NUMBER GENERATED BY THE ADC WHICH IS PROPORTIONAL
*           TO THE CURRENT BETWEEN THE PROBES
*
*     CNT = 128 = 0 VOLTS = NO CURRENT
*
*     + CNT = A NUMBER < 128
*     - CNT = A NUMBER > 128
*
*     %TREATMENT = (128 - CNT) / IOMAX       : FOR + WAVEFORM
*     %TREATMENT = (CNT - 128) / IOMAX       : FOR - WAVEFORM
*
*     VALID VALUES FOR IOMAX:
*
*              20 uAMPS = 3         100 uAMPS = 14
*              30 uAMPS = 4         200 uAMPS = 26
*              40 uAMPS = 5         300 uAMPS = 38
*              50 uAMPS = 6         400 uAMPS = 51
*              60 uAMPS = 8         500 uAMPS = 64
*              70 uAMPS = 9         600 uAMPS = 77
*              80 uAMPS = 10
*              90 uAMPS = 11
* ----------------------------------------------------------
*
*
E3CE  B7 A0 07  A_TO_D  STAA   VOLTS          * START A-TO-D
      86 58             LDAA   # IO_CSR       * CURSOR LOCATION TO LS DIGIT OF
      BD E1 B0          JSR    SETCSR         * TREATMENT PERCENTAGE OUTPUT
      BD E0 00          JSR    DELAY1
      7F 00 AA          CLR    TMPACC         * CLEAR TEMPORARY ACCUMULATOR
      F6 A0 07          LDAB   VOLTS          * GET ADC OUTPUT
      86 80             LDAA   # 80           * ZERO VOLTS ON ADC
      10                SBA                   * ASSUME + WAVE; 80 - ADC CNT
```

```
7D 00 8D         TST    INCVAL      * IS IT A + WAVE?
27 01            BEQ    ATOD1
40               NEGA               * YES, THEN MAKE IT ADC CNT - 80
4D        ATOD1  TSTA
2A 01            BPL    ATOD2       * IF io NOT POSITIVE...
4F               CLRA               * SET TO 0
91 A9     ATOD2  CMPA   IOMAX+1     * IS CURRENT ABOVE MAXIMUM?
2E 34            BGT    OVER_I
91 8F            CMPA   LASMAX      * IS THIS CURRENT ) ANY OTHERS?
23 DA            BLS    A_TO_D
97 8F            STAA   LASMAX      * YES, UPDATE LAST MAX READING
C6 64     DIV0   LDAB   # 64        * YES, THEN CONVERT TO %
3D               MUL                * TIMES 100 (DECIMAL)
7C 00 AA  DIV1   INC    TMPACC
93 A8            SUBD   IOMAX
24 F9            BCC    DIV1
7A 00 AA         DEC    TMPACC      * RESTORE LAST SUBTRACT
C6 0A            LDAB   # 0A        * CONVERT % TO DECIMAL #
96 AA     DIV2   LDAA   TMPACC
7F 00 AA         CLR    TMPACC
7C 00 AA  DIV3   INC    TMPACC
10               SBA
24 FA            BCC    DIV3
7A 00 AA         DEC    TMPACC
1B               ABA                * ACCA CONTAINS LS DIGIT
8A 30            ORAA   # 30        * CONVERT TO ASCII
BD E1 D8         JSR    OUTCHR
D1 AA            CMPB   TMPACC      * IS REMAINDER ) 10?
2F E8            BLE    DIV2
96 AA            LDAA   TMPACC      * NO, SO OUTPUT MS DIGIT
8A 30            ORAA   # 30        * CONVERT TO ASCII
BD E1 D8         JSR    OUTCHR
20 AA            BRA    A_TO_D      * REPEAT UNTIL TIME = 00:00
*
*
*
E426 0F    OVER_I  SEI              * DISABLE ALL MASKABLE INTERRUPTS
CC 02 00           LDD    # 200     * TURN OFF VOLTAGE
BD E1 EB           JSR    OUTDAC
86 3C              LDAA   # 3C      * DISABLE CLOCK INTERRUPTS
B7 00 03           STAA   PORT3C
4F                 CLRA             * DISABLE TIMER INTERRUPTS
97 08              STAA   T_CTRL
BD E0 43           JSR    CSRRHT    * SET CURSOR DIRECTION = RIGHT
CE FD 66           LDX    # EMSG_%  * POINT TO OVER CURRENT MESSAGE
BD E1 B6           JSR    OUT2RW
BD E1 89           JSR    BEEP      * ALERT OPERATOR
BD E0 13  OVERI1   JSR    KEYSCN    * WAIT FOR OPERATOR TO ACKNOWLEDGE
81 E1              CMPA   # CLEARC  * BY PUSHING THE CLEAR KEY
26 F9              BNE    OVERI1
7E E1 FF           JMP    START
*
*
*       THIS ROUTINE CHANGES THE DISPLAYED CLOCK TIME
*       AND CHECKS TO SEE IF ZERO. IF SO IT STOPS THE
*       GENERATION OF THE WAVEFORM.
```

```
E449  B6 80 02  CTIME   LDAA    PORT3D          * CLR INTERRUPT FROM TIMER
      CE 00 90          LDX     # INBUF         * POINT TO BUFFER WITH DISPLAYED TIME IN IT
      A6 00             LDAA    0,X             * GET SECONDS
      81 30             CMPA    # 30            * IS IT ZERO?
      27 12             BEQ     CHK10S
      80 01             SUBA    # 01            * NO, SUBTRACT ONE SECOND
      A7 00     CTIME1  STAA    0,X
      86 19             LDAA    # CK_CSR        * GET CURSOR POSITION OF TIME DISPLAY
      BD E1 C9          JSR     COUTS           * AND RE-DISPLAY NEW TIME
E468  86 58             LDAA    # 58            * SET CURSOR TO % MESSAGE LOC
      BD E1 B0          JSR     SETCSR
      BD E0 00          JSR     DELAY1
      3B                RTI                     * DONE!
      A6 01     CHK10S  LDAA    1,X             * UNITS = 0; GET 10'S OF SECONDS
      81 30             CMPA    # 30            * 10'S = ZERO?
      27 08             BEQ     CHK1M
      80 01             SUBA    # 01            * NO, SUBTRACT TEN SECONDS
      A7 01     CTIME2  STAA    1,X
      86 39             LDAA    # 39            * AND SET UNITS TO 9
      20 E2             BRA     CTIME1
      A6 03     CHK1M   LDAA    3,X             * 10'S = 0; GET UNITS OF MINUTES
      81 20             CMPA    # 20            * IS IT A ASCII SPACE?
      27 1A             BEQ     CTIME4          * YES, THEN DONE
      81 30             CMPA    # 30            * NO, IS IT = 0?
      27 08             BEQ     CHK10M
      80 01             SUBA    # 01            * NO, SUBTRACT 1 MINUTE
      A7 03     CTIME3  STAA    3,X
      86 35             LDAA    # 35            * AND SET 10'S SECONDS = 5
      20 E8             BRA     CTIME2
      A6 04     CHK10M  LDAA    4,X             * GET 10'S OF MINUTES DIGIT
      81 30             CMPA    # 30            * IS IT = 0 OR ASCII SPACE?
      23 08             BLS     CTIME4
      80 01             SUBA    # 01            * NO, SUBTRACT 10 MINUTES
      A7 04             STAA    4,X
      86 39             LDAA    # 39            * AND SET MINUTES = 9
E495  20 EC             BRA     CTIME3
*
*       TIME = 00:00 - STOP THE TREATMENT
*
E497  0F        CTIME4  SEI                     * DISABLE ALL MASKABLE INTERRUPTS
      CC 02 00          LDD     # 200           * TURN OFF VOLTAGE
      BD E1 EB          JSR     OUTDAC
      86 3C             LDAA    # 3C            * DISABLE CLOCK INTERRUPTS
      B7 80 03          STAA    PORT3C
      4F                CLRA                    * DISABLE TIMER INTERRUPTS
      97 08             STAA    T_CTRL
      BD E0 43          JSR     CSRRHT          * SET CURSOR DIRECTION = RIGHT
      CE FD 2C          LDX     # FINMSG        * POINT TO FINISHED MESSAGE
      BD E1 B6          JSR     OUT2RW
      BD E1 89          JSR     BEEP            * ALERT OPERATOR
      BD E0 13  CTIME5  JSR     KEYSCN          * WAIT FOR OPERATOR TO ACKNOWLEDGE
      81 E1             CMPA    # CLEARC        * BY PUSHING THE CLEAR KEY
      26 F9             BNE     CTIME5
      7E E1 FF          JMP     START
E4BC
*
```

```
*       VOLTAGE TABLES
*
        ORG     $ E700
*
E700    SQR_40  DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,01,60,00,01,60,00
                DB      01,60,00,01,60,00,01,60,00,6D,D8,82
*
*
*
E967    SQR_50  DB
*
*
*
        ORG     $ F000
*
F000    MOD_40  DB      01,41,00,01,42,00,01,42,00,01,42,00,01,43,00
                DB      01,43,00,01,43,00,01,44,00,01,44,00,01,44,00
```

```
        DB      01,45,00,01,45,00,01,45,00,01,46,00,01,46,00
        DB      01,47,00,01,47,00,01,47,00,01,48,00,01,48,00
        DB      01,48,00,01,49,00,01,49,00,01,4A,00,01,4A,00
        DB      01,4B,00,01,4B,00,01,4B,00,01,4C,00,01,4C,00
        DB      01,4D,00,01,4D,00,01,4E,00,01,4E,00,01,4E,00
        DB      01,4F,00,01,4F,00,01,50,00,01,50,00,01,51,00
        DB      01,51,00,01,52,00,01,52,00,01,53,00,01,53,00
        DB      01,54,00,01,54,00,01,55,00,01,56,00,01,56,00
        DB      01,57,00,01,57,00,01,58,00,01,58,00,01,59,00
        DB      01,5A,00,01,5A,00,01,5B,00,01,5B,00,01,5C,00
        DB      01,5D,00,01,5D,00,01,5E,00,01,5F,00,01,5F,00
        DB      01,60,00,01,61,00,01,61,00,01,62,00,01,63,00
        DB      01,64,00,01,64,00,01,65,00,01,66,00,01,67,00
        DB      01,67,00,01,68,00,01,69,00,01,6A,00,01,6B,00
        DB      01,6C,00,01,6C,00,01,6D,00,01,6E,00,01,6F,00
        DB      01,70,00,01,71,00,01,72,00,01,73,00,01,74,00
        DB      01,75,00,01,76,00,01,77,00,01,78,00,01,79,00
        DB      01,7A,00,01,7C,00,01,7D,00,01,7E,00,01,7F,00
        DB      01,80,00,01,82,00,01,83,00,01,84,00,01,85,00
        DB      01,87,00,01,88,00,01,8A,00,01,8B,00,01,8C,00
        DB      01,8E,00,01,8F,00,01,91,00,01,93,00,01,94,00
        DB      01,96,00,01,98,00,01,99,00,01,9B,00,01,9D,00
        DB      01,9F,00,01,A1,00,01,A3,00,01,A5,00,01,A7,00
        DB      01,A9,00,01,AB,00,01,AD,00,01,AF,00,01,B2,00
        DB      01,B4,00,01,B7,00,01,B9,00,01,BC,00,01,BE,00
        DB      01,C1,00,01,C4,00,01,C7,00,01,CA,00,01,CD,00
        DB      01,D0,00,01,D3,00,01,D7,00,01,DA,00,01,DE,00
        DB      01,E1,00,01,E5,00,01,E9,00,01,ED,00,01,F2,00
        DB      01,F6,00,01,FB,00,01,00,01,01,05,01,01,0A,01
        DB      01,0F,01,01,15,01,01,1A,00,01,21,01,01,27,01
        DB      01,2D,01,01,34,01,01,3C,01,01,43,01,01,4B,01
        DB      01,54,01,01,5C,01,01,66,01,01,6F,01,01,7A,01
        DB      01,85,01,01,90,01,01,9D,01,01,AA,01,01,B7,01
        DB      01,C6,01,01,D6,01,01,E7,01,01,FA,01,01,0F,02
        DB      01,23,02,01,3A,02,01,53,02,01,6F,02,01,8D,02
        DB      01,AE,02,01,D3,02,01,D8,02,01,D8,02,01,D8,02
        DB      01,D8,02,01,D8,02,01,D8,02,01,D8,02,01,D8,02
        DB      01,D8,02,02,D8,02,02,D8,02,02,D8,02,03,D8,02
        DB      04,D8,02,05,D8,02,07,D8,02,0B,D8,02,28,D8,02

F267
 *
 *
 *
F300 MOD_50 DB  01,3C,00,01,3C,00,01,3C,00,01,3D,00,01,3D,00
        DB      01,3D,00,01,3D,00,01,3E,00,01,3E,00,01,3E,00
        DB      01,3E,00,01,3F,00,01,3F,00,01,3F,00,01,3F,00
        DB      01,40,00,01,40,00,01,40,00,01,40,00,01,41,00
        DB      01,41,00,01,41,00,01,42,00,01,42,00,01,42,00
        DB      01,42,00,01,43,00,01,43,00,01,43,00,01,44,00
        DB      01,44,00,01,44,00,01,44,00,01,45,00,01,45,00
        DB      01,45,00,01,46,00,01,46,00,01,46,00,01,47,00
        DB      01,47,00,01,47,00,01,48,00,01,48,00,01,48,00
        DB      01,49,00,01,49,00,01,49,00,01,4A,00,01,4A,00
        DB      01,4A,00,01,4B,00,01,4B,00,01,4C,00,01,4C,00
        DB      01,4C,00,01,4D,00,01,4D,00,01,4E,00,01,4E,00
        DB      01,4E,00,01,4F,00,01,4F,00,01,50,00,01,50,00
        DB      01,50,00,01,51,00,01,51,00,01,52,00,01,52,00
```

```
              DB    01,53,00,01,53,00,01,53,00,01,54,00,01,54,00
              DB    01,55,00,01,55,00,01,56,00,01,56,00,01,57,00
              DB    01,57,00,01,58,00,01,58,00,01,59,00,01,59,00
              DB    01,5A,00,01,5A,00,01,5B,00,01,5B,00,01,5C,00
              DB    01,5D,00,01,5D,00,01,5E,00,01,5E,00,01,5F,00
              DB    01,5F,00,01,60,00,01,61,00,01,61,00,01,62,00
              DB    01,63,00,01,63,00,01,64,00,01,64,00,01,65,00
              DB    01,66,00,01,67,00,01,67,00,01,68,00,01,69,00
              DB    01,69,00,01,6A,00,01,6B,00,01,6C,00,01,6C,00
              DB    01,6D,00,01,6E,00,01,6F,00,01,6F,00,01,70,00
              DB    01,71,00,01,72,00,01,73,00,01,74,00,01,75,00
              DB    01,75,00,01,76,00,01,77,00,01,78,00,01,79,00
              DB    01,7A,00,01,7B,00,01,7C,00,01,7D,00,01,7E,00
              DB    01,7F,00,01,80,00,01,81,00,01,82,00,01,84,00
              DB    01,85,00,01,86,00,01,87,00,01,88,00,01,89,00
              DB    01,8B,00,01,8C,00,01,8D,00,01,8F,00,01,90,00
              DB    01,91,00,01,93,00,01,94,00,01,96,00,01,97,00
              DB    01,99,00,01,9A,00,01,9C,00,01,9D,00,01,9F,00
              DB    01,A1,00,01,A2,00,01,A4,00,01,A6,00,01,A8,00
              DB    01,A9,00,01,AB,00,01,AD,00,01,AF,00,01,B1,00
              DB    01,B3,00,01,B5,00,01,B8,00,01,BA,00,01,BC,00
              DB    01,BE,00,01,C1,00,01,C3,00,01,C6,00,01,C8,00
              DB    01,CB,00,01,CE,00,01,D0,00,01,D3,00,01,D6,00
              DB    01,D9,00,01,DC,00,01,E0,00,01,E3,00,01,E6,00
              DB    01,EA,00,01,ED,00,01,F1,00,01,F5,00,01,F9,00
              DB    01,FD,00,01,01,01,01,06,01,01,0A,01,01,0F,01
              DB    01,14,01,01,19,01,01,1E,01,01,23,01,01,29,01
              DB    01,2F,01,01,35,01,01,3B,01,01,42,01,01,49,01
              DB    01,50,01,01,57,01,01,5F,01,01,67,01,01,70,01
              DB    01,79,01,01,82,01,01,8C,01,01,97,01,01,A2,01
              DB    01,AE,01,01,BA,01,01,C7,01,01,D5,01,01,E3,01
              DB    01,F3,01,01,04,02,01,16,02,01,29,02,01,3D,02
              DB    01,54,02,01,6C,02,01,85,02,01,A2,02,01,C0,02
              DB    01,D8,02,01,D8,02,01,D8,02,01,D8,02,01,D8,02
              DB    01,D8,02,01,D8,02,01,D8,02,01,D8,02,01,D8,02
              DB    01,D8,02,02,D8,02,02,D8,02,02,D8,02,03,D8,02
              DB    03,D8,02,04,D8,02,05,D8,02,07,D8,02,0B,D8,02
              DB    1A,D8,02,

*
    *
    *

F600  MOD_60  DB    01,35,00,01,35,00,01,35,00,01,35,00,01,35,00
              DB    01,35,00,01,36,00,01,36,00,01,36,00,01,36,00
              DB    01,36,00,01,37,00,01,37,00,01,37,00,01,37,00
              DB    01,37,00,01,37,00,01,38,00,01,38,00,01,38,00
              DB    01,38,00,01,38,00,01,39,00,01,39,00,01,39,00
              DB    01,39,00,01,39,00,01,3A,00,01,3A,00,01,3A,00
              DB    01,3A,00,01,3B,00,01,3B,00,01,3B,00,01,3B,00
              DB    01,3B,00,01,3C,00,01,3C,00,01,3C,00,01,3C,00
              DB    01,3D,00,01,3D,00,01,3D,00,01,3D,00,01,3D,00
              DB    01,3E,00,01,3E,00,01,3E,00,01,3E,00,01,3F,00
              DB    01,3F,00,01,3F,00,01,3F,00,01,40,00,01,40,00
              DB    01,40,00,01,40,00,01,41,00,01,41,00,01,41,00
              DB    01,41,00,01,42,00,01,42,00,01,42,00,01,43,00
              DB    01,43,00,01,43,00,01,43,00,01,44,00,01,44,00
              DB    01,44,00,01,45,00,01,45,00,01,45,00,01,45,00
```

```
       DB    01,46,00,01,46,00,01,46,00,01,47,00,01,47,00
       DB    01,47,00,01,48,00,01,48,00,01,48,00,01,49,00
       DB    01,49,00,01,49,00,01,4A,00,01,4A,00,01,4A,00
       DB    01,4B,00,01,4B,00,01,4B,00,01,4C,00,01,4C,00
       DB    01,4C,00,01,4D,00,01,4D,00,01,4D,00,01,4E,00
       DB    01,4E,00,01,4F,00,01,4F,00,01,4F,00,01,50,00
       DB    01,50,00,01,51,00,01,51,00,01,51,00,01,52,00
       DB    01,52,00,01,53,00,01,53,00,01,53,00,01,54,00
       DB    01,54,00,01,55,00,01,55,00,01,56,00,01,56,00
       DB    01,57,00,01,57,00,01,58,00,01,58,00,01,59,00
       DB    01,59,00,01,59,00,01,5A,00,01,5A,00,01,5B,00
       DB    01,5C,00,01,5C,00,01,5D,00,01,5D,00,01,5E,00
       DB    01,5E,00,01,5F,00,01,5F,00,01,60,00,01,60,00
       DB    01,61,00,01,62,00,01,62,00,01,63,00,01,63,00
       DB    01,64,00,01,65,00,01,65,00,01,66,00,01,67,00
       DB    01,67,00,01,68,00,01,69,00,01,69,00,01,6A,00
       DB    01,6B,00,01,6B,00,01,6C,00,01,6D,00,01,6E,00
       DB    01,6E,00,01,6F,00,01,70,00,01,71,00,01,71,00
       DB    01,72,00,01,73,00,01,74,00,01,75,00,01,75,00
       DB    01,76,00,01,77,00,01,78,00,01,79,00,01,7A,00
       DB    01,7B,00,01,7C,00,01,7D,00,01,7E,00,01,7F,00
       DB    01,80,00,01,81,00,01,82,00,01,83,00,01,84,00
       DB    01,85,00,01,86,00,01,87,00,01,88,00,01,89,00
       DB    01,8B,00,01,8C,00,01,8D,00,01,8E,00,01,90,00
       DB    01,91,00,01,92,00,01,93,00,01,95,00,01,96,00
       DB    01,98,00,01,99,00,01,9B,00,01,9C,00,01,9E,00
       DB    01,9F,00,01,A1,00,01,A2,00,01,A4,00,01,A6,00
       DB    01,A7,00,01,A9,00,01,AB,00,01,AD,00,01,AE,00
       DB    01,B0,00,01,B2,00,01,B4,00,01,B6,00,01,B8,00
       DB    01,BB,00,01,BD,00,01,BF,00,01,C1,00,01,C4,00
       DB    01,C6,00,01,C8,00,01,CB,00,01,CD,00,01,D0,00
       DB    01,D3,00,01,D6,00,01,D8,00,01,DB,00,01,DE,00
       DB    01,E1,00,01,E5,00,01,E8,00,01,EB,00,01,EF,00
       DB    01,F2,00,01,F6,00,01,FA,00,01,FE,00,01,02,01
       DB    01,06,01,01,0A,01,01,0E,01,01,13,01,01,18,01
       DB    01,1D,01,01,22,01,01,27,01,01,2C,01,01,32,01
       DB    01,38,01,01,3E,01,01,44,01,01,4B,01,01,52,01
       DB    01,59,01,01,61,01,01,68,01,01,71,01,01,79,01
       DB    01,82,01,01,8B,01,01,95,01,01,A0,01,01,AA,01
       DB    01,B6,01,01,C2,01,01,CF,01,01,DC,01,01,EB,01
       DB    01,FA,01,01,0A,02,01,1C,02,01,2E,02,01,42,02
       DB    01,57,02,01,6E,02,01,87,02,01,A2,02,01,BF,02
       DB    01,D8,02,01,D8,02,01,D8,02,01,D8,02,01,D8,02
       DB    01,D8,02,01,D8,02,01,D8,02,01,D8,02,01,D8,02
       DB    01,D8,02,02,D8,02,02,D8,02,02,D8,02,02,D8,02
       DB    03,D8,02,03,D8,02,04,D8,02,05,D8,02,07,D8,02
       DB    0A,D8,02,14,D8,02
*
F999
*
*
*
       ORG   $FB00
*
*    NON-MASKABLE INTERRUPT HANDLER
*
```

```
FB00  CC 02 00       LDD    # 200        * SHUT OFF VOLTAGE
      BD E1 EB       JSR    OUTDAC
      BD E0 00       JSR    DELAY2
      BD E0 43       JSR    CSRRHT       * SET CURSOR MOVE DIR = RIGHT
      CE FC 2F       LDX    # EMSG_I     * PRINT INTERRUPT MESSAGE
      BD E1 B6       JSR    OUT2RW
      BD E1 89       JSR    BEEP
      BD E0 13  NMI1 JSR    KEYSCN       * WAIT FOR CLEAR KEY
      81 E1          CMPA   # CLEARC
      26 F9          BNE    NMI1
```

What is claimed is:

1. A treatment method of increasing the metabolic activity of preselected cells in living animal tissue including the steps of:
   A. situating a pair of spaced-apart electrodes in contact with healthy animal tissue on opposite sides of an area containing cells to be treated; and
   B. externally inducing a percutaneous flow of electrical current between said electrodes through said area by impressing an external bipolar voltage wave form across said electrodes at a frequency of between 0.1 and 1.0 Hz.

2. The method of claim 1 including the step of:
   C. monitoring the current between said electrodes and adjusting the voltage wave impressed between the electrodes so that the current flow resulting from performance with Step B does not at any time exceed 900 microamperes.

3. The method of claim 2 including the step of:
   D. confining the maximum flow of current between the electrodes in Step B to a range between 20 and 900 microamperes.

4. The method of claim 2 including the step of:
   D. controlling the frequency of the voltage wave impressed across the electrodes in Step B to between 0.1 and 1.0 Hz.

5. The method of claim 4 including the step of:
   E. selecting the wave form of the voltage impressed in Step B from among wave forms which when impressed on the electrodes according to the method of the claim will produce no insult to the animal tissue being treated.

6. The method of claim 4 including the steps of:
   E. continuing the externally induced flow of electrical current between the electrodes and through the area containing cells to be treated for a predetermined treatment activation period;
   F. terminating the current flow after the activation period;
   G. repositioning the electrodes in contact with healthy tissue in adjacent but spaced relation to the area containing cells to be treated to provide a different path for current flow between the electrodes; and
   H. repeating steps A–G until all portions of the area to be treated have been treated by current flow between the electrodes.

7. The method of claim 6 including the step of:
   I. controlling the treatment activation period of induced current flow for each positioning of the electrodes to not less than 20 seconds.

8. The method of claim 7 including the step of:
   J. limiting the activation period of induced current flow to not more than 20 minutes.

9. A treatment method of increasing the metabolic activity of preselected cells adjacent to damaged cells in living animal tissue and of reducing the concentration of free radicals adjacent the damaged cells resulting from the damage to those cells, said method including the steps of:
   A. situating a pair of spaced-apart electrodes in contact with the living tissue on opposite sides of cells to be treated and in spaced, relatively close adjacent relation to such damaged cells;
   B. inducing a percutaneous bipolar flow of current between said electrodes by impressing a bipolar voltage wave form across the electrodes; and
   C. monitoring the power level between the electrodes to assure that a power level of the current and voltage is at all times insufficient to damage said cells.

10. An electrical medical treatment instrument for increasing metabolic activity of preselected cells of living tissue, said instrument including:
    A. a source of direct electrical energy;
    B. a pair of output terminals;
    C. means for generating from said energy source a voltage wave of predetermined shape and magnitude and impressing it across said output terminals, said voltage wave being such as to never generate a power level sufficient to damage the preselected cells being treated, and being of a frequency and form which will not insult living tissue when impressed across adjacent areas of said tissue;
    D. a pair of electrodes adapted to be positioned in spaced relation to each other, in contact with said tissue on opposite sides of, and spaced from, said cells to be treated, and each being electrically connected to one of said output terminals to induce percutaneous electron flow in said tissue; and E. means to limit the flow of current in said tissue to less than that which can damage the cells being treated.

11. An electrical medical instrument for increasing metabolic activity of preselected cells of living tissue by producing an electrical treatment signal adapted for application to the tissue to thereby induce percutaneous electric current flow through the cells to be treated, including:

A. means for producing a plurality of periodic electrical treatment signals at a treatment signal frequency, each for a treatment signal time period, the treatment signal being characterized by first and second electrical parameters;

B. means for receiving information representative of a selected value of the first electrical parameter of the treatment signal;

C. means for monitoring the first electrical parameter of the treatment signal; and D. means responsive to the means for receiving information and the means for monitoring the first electrical parameter for causing the second parameter of the treatment signal to increase during each treatment signal time period until the first parameter of the treatment signal attains the selected value, and for maintaining the first parameter of the treatment signal at the selected value for a remainder of each such period.

12. The instrument of claim 11 wherein:

A.(1) the means for producing treatment signals causes the first electrical parameter to be current of the treatment signals; and (2) the means for producing the treatment signals causes the second electrical parameter to be voltage of the treatment signals.

13. The instrument of claim 12 wherein:

A.(1)(a) the means for producing the treatment signals causes magnitude of the current of the treatment signals to be within a range of about 20 to 900 microamperes.

14. The instrument of claim 12 wherein:

A.(2)(a) the means for producing the treatment signals causes magnitude of the voltage of the treatment signal to be within a range of about 0 to 30 volts.

15. The instrument of claim 11 wherein:

A.(1) the means for producing the treatment signals produces a bipolar wave of treatment signals.

16. The instrument of claim 11 and further incuding:

E. means for receiving information representative of a selected treatment signal frequency, connected to the means for producing the treatment signal to cause the treatment signals to have the selected treatment signal frequency.

17. The instrument of claim 16 and further including:

F. means connected to the medical instrument for prompting a clinician to enter the information representative of the selected treatment signal frequency.

18. The instrument of claim 17 and further including:

G. means connected to the medical instrument for producing a visual display of the selected treatment signal frequency.

19. The instrument of claim 11 wherein:

A.(1) the means for producing the treatment signal causes the treatment signal frequency to be within a range of about 0.1 to about 0.9 Hz.

20. The instrument of claim 11 and further including:

E. means for receiving information representative of a selected activation time period, connected to the means for producing the treatment signals to cause the treatment signals to be produced for the selected activation time period.

21. The instrument of claim 20 and further including:

F. means for prompting a clinician to enter the information representative of the selected activation time period.

22. The instrument of claim 21 and further including:

G. means for producing a visual display of selected activation time period.

23. The instrument of claim 11 wherein:

A.(1) means for producing the treatment signal causes the activation time period to be within a range of about 20 seconds to about 20 minutes.

24. The instrument of claim 11 and further including:

E. means for prompting a clinician to enter the information representative of the first electrical parameter.

25. The instrument of claim 24 and further including:

F. means for providing a visual display of the selected value of the first electrical parameter.

26. The instrument of claim 11 wherein:

D.(1) the means for causing the second parameter of each treatment signal to increase causes the second parameter to increase linearly during each treatment signal time period until the first parameter of the treatment signal attains the selected value and causes it to maintain the selected value for the remainder of the treatment signal time period.

27. The instrument of claim 11 wherein:

D.(1) the means for causing the second parameter of each treatment signal to increase causes the second parameter to increase nonlinearly during each treatment signal time period until the first parameter of the treatment signal attains the selected value and causes it to maintain the selected value for the remainder of the treatment signal time period.

28. The instrument of claim 27 wherein:

D.(1)(a) the means for causing the second parameter of each treatment signal to increase causes the second parameter to increase as a function of an exponential during each treatment signal time period until the first parameter of the treatment signal attains the selected value and causes it to maintain the selected value for the remainder of the treatment signal time period.

29. The instrument of claim 28 wherein:

D.(1)(a)(i) the means for causing the second parameter of the treatment signal to increase causes the second parameter of the treatment signal to increase in proportion to an exponential function $(1-e^{-t/K})$ where t is time and K is a constant.

30. The instrument of claim 11 and further including:

E. power supply means connected to the medical instrument; and

F. means connected to the power supply means for providing a visual initialization message when power is first applied to the instrument.

31. The instrument of claim 11 and further including:

E. means connected to the medical instrument for producing a visual display indicative of instrument operation input requirements.

32. The instrument of claim 11 and further including:
E. battery means connected to the medical instrument; and
F. means connected to the battery means for producing a visual display indicative of low battery power.

33. An electrical medical instrument for increasing metabolic activity of preselected cells of living tissue by producing an electrical treatment signal adapted for application to the tissue to thereby induce percutaneous electric current flow through the cells to be treated, including:
A. means for producing a plurality of periodic electrical bipolar treatment signals at a treatment signal frequency, each for a treatment signal time period, the treatment signal being characterized by first and second electrical parameters;
B. means for receiving information representative of a selected value of the first electrical parameter of the treatment signal;
C. means for monitoring the first electrical parameter of the treatment signal;
D. means responsive to the means for receiving information and the means for monitoring the first electrical parameter for causing the second parameter of the treatment signal to increase during each treatment signal time period until the first parameter of the treatment signal attains the selected value, and for maintaining the first parameter of the treatment signal at the selected value for a remainder of each such period;
E. means for preselecting a range of electrical parameters for acceptable operation of the medical instrument; and
F. means for aborting the periodic electrical treatment signals and returning the second parameter of electric treatment signal to zero upon the magnitude of any of the preselected parameters being outside of its preselected range.

* * * * *